(12) United States Patent
Yeates et al.

(10) Patent No.: US 10,688,257 B2
(45) Date of Patent: *Jun. 23, 2020

(54) APPARATUS AND METHOD FOR GENERATING PARTICLE AEROSOLS WITH HELIOX

(71) Applicant: KAER BIOTHERAPEUTICS CORPORATION, Escondido, CA (US)

(72) Inventors: Donovan B Yeates, Escondido, CA (US); Xin Heng, McKinney, TX (US)

( * ) Notice: Subject to any disclaimer, the term of this patent is extended or adjusted under 35 U.S.C. 154(b) by 230 days.

This patent is subject to a terminal disclaimer.

(21) Appl. No.: 15/947,703

(22) Filed: Apr. 6, 2018

(65) Prior Publication Data
US 2018/0221596 A1    Aug. 9, 2018

Related U.S. Application Data

(63) Continuation of application No. 15/291,028, filed on Oct. 11, 2016, now Pat. No. 9,937,303.

(51) Int. Cl.
*A61M 11/00*    (2006.01)
*A61M 11/02*    (2006.01)
(Continued)

(52) U.S. Cl.
CPC ........... *A61M 11/02* (2013.01); *A61M 11/006* (2014.02); *A61M 11/06* (2013.01); *A61M 15/0086* (2013.01); *A61M 16/125* (2014.02); *B05B 7/0416* (2013.01); *F26B 3/12* (2013.01); *A61M 11/002* (2014.02);
(Continued)

(58) Field of Classification Search
CPC ............... A61M 11/02; A61M 16/125; A61M 2202/064; A61M 15/0086; A61M 15/008; A61M 2016/0036; A61M 2205/362; A61M 11/06; B05B 7/0416; B05B 7/065; B01D 45/08
See application file for complete search history.

(56) References Cited

U.S. PATENT DOCUMENTS 4,767,524 A     8/1988   Yeh et al.
6,234,167 B1    5/2001   Cox et al.
(Continued)

OTHER PUBLICATIONS

Non-Final Office Action issued by the United States Patent and Trademark Office in U.S. Appl. No. 15/291,028 dated Aug. 3, 2017.
(Continued)

*Primary Examiner* — Steven O Douglas
(74) *Attorney, Agent, or Firm* — Alexander R. Schlee; Schlee IP International, PC

(57) ABSTRACT

A system and a method for generating a respirable dry powder aerosol (15) from a liquid solution or liquid suspension at a respirable dry powder aerosol volume flow (91). A liquid aerosol generating nozzle (3) generates from the liquid solution or liquid suspension a liquid aerosol (13) that is diluted by dilution gas (4) and dried in a cylindrical evaporation chamber (6) to generate a dry powder aerosol (14) that is subsequently concentrated. The system and method may include heliox as a gas, specifically dilution gas (4), for enhancing both the drying process in the cylindrical evaporation chamber (6) and for enhancing the concentration efficiency, but also as a nozzle gas (2) for enhancing generating the liquid aerosol (13) from the liquid solution or liquid suspension.

27 Claims, 10 Drawing Sheets

(51) Int. Cl.
*A61M 16/12* (2006.01)
*B05B 7/04* (2006.01)
*A61M 15/00* (2006.01)
*A61M 11/06* (2006.01)
*F26B 3/12* (2006.01)

(52) U.S. Cl.
CPC .............. *A61M 2202/0208* (2013.01); *A61M 2202/0488* (2013.01); *A61M 2202/064* (2013.01)

(56) References Cited

U.S. PATENT DOCUMENTS

| | | |
|---|---|---|
| 6,491,233 B2 | 12/2002 | Nichols |
| 6,779,520 B2 | 8/2004 | Genova et al. |
| 7,708,011 B2 | 5/2010 | Hochrainer et al. |
| 8,375,987 B2 | 2/2013 | Yeates |
| 8,596,268 B2 | 12/2013 | Yeates |
| 8,616,532 B2 | 12/2013 | Yeates |
| 8,820,662 B2 | 9/2014 | Yeates |
| 9,573,147 B1 | 2/2017 | Yeates |
| 2011/0006129 A1 | 1/2011 | Yeates |
| 2013/0074842 A1 | 3/2013 | Boucher |

OTHER PUBLICATIONS

Reply filed Nov. 3, 2017 to the Non-Final Office Action dated Aug. 3, 2017 by the United States Patent and Trademark Office in U.S. Appl. No. 15/291,028.
Notice of Allowance issued by the United States Patent and Trademark Office for U.S. Appl. No. 15/291,028 dated Nov. 30, 2017.

Section I-I

Section F-F

DETAIL A

Section D-D

Section G-G

Section A-A

APPARATUS AND METHOD FOR GENERATING PARTICLE AEROSOLS WITH HELIOX

CROSS-REFERENCE TO RELATED APPLICATIONS

This application is a Continuation application claiming the benefit of the United States parent patent application Ser. No. 15/291,028, the content of which is herewith incorporated by reference.

GOVERNMENT SUPPORT

The present invention, in part, was supported by the National Institutes of Health, Heart, Lung and Blood Institute under grant R43HL127834. The US government has certain rights to this invention.

BACKGROUND OF THE INVENTION

The acute respiratory distress syndrome, ARDS, occurs in approximately 200,000 Americans each year. A recent worldwide study indicated that ARDS is an underdiagnosed with 10.4% of all patients admitted to the intensive care unit, ICU, fulfilling the ARDS criteria. The pathology includes atelectasis, pulmonary edema, elevated pulmonary dead space and hypoxemia. Despite sophisticated intensive care, many patients with milder hypoxemia (PaO2/FiO2 between 200 and 300 mmHg) deteriorate to ARDS with a PaO2/FiO2<200 mmHg. Despite improved low tidal volume ventilation maintenance the mortality rate still remains at 30-40%.

Although the etiology of ARDS is often multifactorial, common to patients with ARDS is impaired surfactant function and continued inflammation-induced degradation of surfactant's surface tension lowering activity. The volume of aerated lung available for gas exchange and mechanical insufflation is reduced as a result of dense atelectasis predominantly in dependent lung regions. Surfactant's low surface tension helps maintain the patency of the conducting airways and enables the alveoli to open with a reduced work of breathing. Thus aerosol surfactant replacement therapy may provide a life saving treatment regime.

Clinical trials with surfactant aerosols for the treatment of ARDS however, have not shown the anticipated clinical benefit of surfactant administration. Contributing factors to this outcome include:

Insufficient surfactant delivery rate to the lungs
Surfactant not being administered throughout the prolonged surfactant abnormality.

The delivery of surfactant in a non-invasive manner would allow physicians to provide improved life support and potentially a marked improvement in survival.

Aerosol delivery of surfactant to the lungs may benefit other patients with compromised lung function. This includes the treatment of patients with idiopathic pulmonary fibrosis that has a prevalence rate of 13-20/100,000 population or ~60,000 patients in the US. In addition, aerosols of surfactant may have therapeutic benefits in patients with neonatal respiratory distress syndrome, NRDS, chronic obstructive pulmonary disease, asthma, cystic fibrosis, and pneumonia. Hospital acquired respiratory infections are a major heath issue and cost an estimated $6 B annually. Treatment of such respiratory infections with anti-infectives by respirable aerosol delivery by systems such as SUPRAER™ could reduce these health costs. Also, it would be an improvement over the prior art if epoprostenol, mucoactive agents and other medications which form solutions or suspensions could be delivered at high delivery rates with viscosities up to at least 39 cSt in a clinical setting. In addition, co-delivery of surfactant with drugs may augment the effectiveness of these drugs.

Biologics are 50% of the drug development pipeline. At least 60 of these are in development for the treatment of lung diseases that are targeted to be delivered intravenously rather than by aerosol. The IV route is most often chosen for the treatment of lung disease with biologics due to the limitations of present aerosol delivery systems and inbuilt perceptions within the pharmaceutical industry. However, intravenous administration not only has considerable patient resistance, but its own attendant complications. Intravenous administration is likely to require a 10 to 100 times higher dose than if it were administered by aerosol inhalation. The ability to deliver these agents directly to the lungs in form of respirable aerosol markedly reduces the total dose of the agent, the cost of therapy, as well as systemic toxicities.

Non-small-cell lung cancer is treated with cocktails of drugs delivered intravenously. Twenty four biologics for lung cancer are in clinical trials and 12 in the market.

With IV administration:
2-15% treats the lungs
>85% exposes other organs
Dose 10-100 times that of aerosol inhalation
Aerosol delivery results in;
Lower doses administered
Less systemic side-effects
Lower treatment costs and potentially better outcomes.

An estimate of effective dose of surfactant delivered by aerosol in patients with ARDS provides guidance as to the dose rate and total dose of surfactant aerosol that is necessary to be delivered by an aerosolizing device. Delivery of 2-7.5 mg/kg of surfactant aerosol has been shown to be effective in neonatal lambs. Windtree Therapeutics delivered 100 mg/hour or 0.03 mg/s of aerosolized surfactant to neonates but it is considered likely that only a small percentage of this was delivered to the lungs. In ARDS there is inactivation of the surfactant by proteins and phospholipases and thus a higher dose delivered to the lungs may be desirable. The mass of surfactant in healthy lungs has been estimated to be 5-10 mg/kg. Thus total surfactant replacement in a 70 kg patient will require 350-700 mg to be deposited in the lungs. Thus, clinically relevant therapeutic doses between 300 mg and 1 g of surfactant aerosol deposited in the lungs are likely required for efficacy. Due to continued inflammation-induced degradation of surfactant in this aerosol surfactant replacement therapy may be required to be repeated on multiple occasions.

Delivery of a sufficient mass of aerosolized surfactant of aerosols between 1.5 µm and 4 µm mass median aerodynamic diameter to penetrate to and deposit in the peripheral lung to treat surfactant abnormalities and its continued depletion has been a recalcitrant problem for many years. There are several issues to be overcome related to aerosol particle size, dose rate and uniformity of dose rate as well as the concentration of the aerosol and total dose output.

The output of jet-type nebulizers that produce 3 µm particles and rely on the Venturi effect for the fluid feed to the orifice produce is low (≤3 ml/min) and decreases with increasing fluid viscosity (surfactant concentration). The concentration of surfactant in the device increases with atomization time. In addition, foaming can further reduce their output.

The viscosity of surfactant suspensions increases rapidly with surfactant concentration. High concentrations of surfactant have viscosities considerably higher than some mesh-type nebulizers can aerosolize (4 cP) It took 3 hours to deliver 72 mg of a surfactant aerosol at 1.9 µm MMAD.

An aerosol delivery system has been used by Windtree Therapeutics to deliver aerosolized surfactant to neonates. In this system, described in U.S. Pat. No. 6,234,167 B1, a surfactant suspension is heated and vaporized as it passes through a capillary tube. The condensate forms the aerosol to be delivered. In clinical trials of this system in neonates it produces 100 mg/hour (0.03 mg/s) surfactant aerosol at a flow rate of 3 l/min, i.e. 0.6 mg/l.

A method of generating high concentrations of fine particle aerosols has been described in the U.S. Pat. No. 8,596,268 B2 which is incorporated by reference in its entirety. Briefly, a syringe pump is used to feed an aqueous solution/suspension to an aerosolizing nozzle. This nozzle aerosolizes 100% of the fluid to form a liquid aerosol with a narrow size distribution ($\sigma g < 2$). This aerosol plume is arrested with a co-axial counter-flow of gas. The fluid is evaporated from the particles using a combination of warm compressed gas, and dilution gas together with infrared radiation whose wavelength is optimized for the absorption band of water. The resultant dry particle aerosol is concentrated using a multiple slit virtual impactor with radially aligned acceleration and deceleration nozzles. The particles gain momentum as they pass through the acceleration nozzles. They cross a small gap and lose momentum as they pass through the deceleration nozzles to form a low velocity aerosol. Most of the gas exits the aerosol stream through the gap between these nozzles. As a consequence, the low velocity aerosol is comprised of a considerably higher concentration of particles in a much smaller volume of gas. This aerosol flows through port at 3 cm of water pressure where it can be inhaled on demand. However, for deep lung deposition in patients with compromised lung function aerosols with even smaller diameters at higher delivery rates and high total payloads are desirable to treat patients with ARDS and other lung syndromes and diseases. It is therefore an object of the invention to produce smaller particles at higher concentrations at higher efficiencies together with high clinically relevant payloads.

Heliox, a mixture of helium and oxygen, typically 80% helium and 20% oxygen or 70% helium and 30% oxygen, has been used to improve the effect of bronchodilators and gas exchange in patients with compromised lung function and enhance aerosol deposition in the peripheral lung and thus offers an attractive option for the delivery of therapeutic aerosols. In studies using 70/30 heliox at constant atomizer gas flow to generate aerosols showed that the heliox generated larger particles than air at all tested flow rates However, using the invention described herein accomplishes a marked decrease in aerosol particle size with heliox compared to air at the same compressed gas pressure.

A number of virtual impactors have been described to concentrate aerosols. For example, some linear slit concentrators use a converging channel with a rectangular "v" shaped design as noted above. The mass loading of an aerosol being concentrated can decrease the efficiency of the concentrator and lead to nozzle clogging above concentrations of 1 mg/l. To deliver very high payloads, the aerosol is likely already at a high concentration prior to it being further concentrated. Aerosol deposition on the surfaces of the concentrator must not impair its function during the generation and delivery of this designated payload. Aerosol concentrators that meet the performance of the incident invention have not been described.

As virtual impactors are dependent on the inertia of the aerosol particles, high efficiencies for concentrating particles less than 4 µm MMAD have be difficult to attain, especially with low pressure differentials. For simplicity and clinical utility, it is desirable when concentrating an aerosol using virtual impaction, that this is accomplished at a small positive pressure together such that it can be delivered to the patient at a slight positive pressure without the use of pumps to remove the exhausted gas. This requirement essentially eliminates the use of virtual impactors with high flow resistance such as those using round orifices. Slit orifices have a much lower resistance to gas flow and are thus used in the incident invention. Aerodynamically designed acceleration and deceleration nozzles reduce resistance to flow and improve the concentrator efficiency. U.S. Pat. No. 8,375,987 meets these requirements and is hereby included in its entirety. However, the incident invention provides for the generation and processing of smaller particles with less wall losses and higher aerosol concentrations that can be delivered at higher payloads.

As noted above, the technology for the delivery of surfactant aerosols for inhalation neither incorporates the technologies of the incident invention nor provides the aerosol concentrations and delivery criteria present in the incident invention.

SUMMARY OF THE INVENTION

It is an object of this invention to create an respirable aerosol generating system and a method for generating such respirable dry powder aerosol generation and processing system that a) generates small diameter particles from a liquid solution or liquid suspension, b) improves heat and mass transfer and thus the rate of evaporation of fluid from a liquid aerosol to subsequently generate a dry powder aerosol having a respirable particles size, c) reduces aerosol wall-losses, d) enhances the efficiency of aerosol concentration, e) has low input to output pressure differential and input to ambient pressure differential and f) realizes high aerosol delivery rates of very fine particles at higher efficiencies and higher payloads than previously attained.

It is an object of this invention to generate and deliver high concentrations of aerosols 1.5-4 µm mass median aerodynamic diameter aerosols at flow rates between 10 and 50 liters per minute minutes using a cylindrical linear single slit virtual impactor with efficiencies greater than 58% with outputs up to at least 2 g while avoiding any sonic resonance.

It is an object of this invention to form a two-stage concentrator that generates high concentrations of 1.5 to 6 µm MMAD aerosols without the use of auxiliary fans or flow controls on the exhaust exit ports of either concentrator.

According to one aspect of the invention, an aerosol generating system for generating a respirable dry powder aerosol from a liquid solution or liquid suspension at a respirable dry powder aerosol volume flow is provided, comprising: a liquid aerosol generating nozzle having a nozzle input end designed to receive the liquid solution or liquid suspension, and having a nozzle gas supply designed to receive nozzle gas, the liquid aerosol generating nozzle further having a nozzle output end for outputting a liquid aerosol suspended in the nozzle gas; a cylindrical evaporation chamber having a cylindrical evaporation chamber input end that is connected to the nozzle output end and connected to a dilution gas supply for receiving both the liquid aerosol suspended in the nozzle gas and for receiving the dilution gas, and the cylindrical evaporation chamber having a cylindrical evaporation chamber output end outputting a first intermediate dry powder aerosol at a first intermediate dry powder aerosol volume flow and a first intermediate dry powder aerosol particle concentration; and a cylindrical single linear slit aerosol concentrator having a cylindrical single linear slit aerosol concentrator input end that is connected to the cylindrical evaporation chamber output end, the cylindrical single linear slit aerosol concentrator comprising a converging cylindrical single linear slit aerosol concentrator input channel converging from the cylindrical single linear slit aerosol concentrator input end to a cylindrical single linear slit aerosol concentrator input orifice that is connected to a cylindrical single linear slit aerosol concentrator aerosol separation space, the cylindrical single linear slit aerosol concentrator aerosol separation space connecting both to a cylindrical single linear slit aerosol concentrator exhaust port and to a cylindrical single linear slit aerosol concentrator output orifice, the cylindrical single linear slit aerosol concentrator output orifice being connected to a diverging cylindrical single linear slit aerosol concentrator output channel outputting the respirable dry powder aerosol at the respirable dry powder aerosol volume flow that is lower than the first intermediate dry powder aerosol volume flow and at a respirable dry powder aerosol particle concentration that is higher than the first intermediate dry powder aerosol particle concentration.

According to another aspect of the invention, a corresponding method provides for generating a respirable dry powder aerosol from a liquid solution or liquid suspension at a respirable dry powder aerosol volume flow, comprising: feeding liquid solution or liquid suspension and nozzle gas into a liquid aerosol generating nozzle; outputting from the liquid aerosol generating nozzle a liquid aerosol suspended in the nozzle gas into a cylindrical evaporation chamber; feeding dilution gas into the cylindrical evaporation chamber; outputting from the cylindrical evaporation chamber a first intermediate dry powder aerosol having fine dry powder particles that allow respirable particles containing a medically active agent and are suspended in gas at a first intermediate dry powder aerosol volume flow and a first intermediate dry powder aerosol particle concentration; feeding the first intermediate dry powder aerosol into a cylindrical single linear slit aerosol concentrator, the cylindrical single linear slit aerosol concentrator comprising a converging cylindrical single linear slit aerosol concentrator input channel converging to a cylindrical single linear slit aerosol concentrator input orifice and a diverging cylindrical single linear slit aerosol concentrator output channel diverging from a cylindrical single linear slit aerosol concentrator output orifice; and outputting the respirable dry powder aerosol at the respirable dry powder aerosol volume flow that is lower than the first intermediate dry powder aerosol volume flow and a respirable dry powder aerosol particle concentration that is higher than the first intermediate dry powder aerosol particle concentration.

According to other aspects of the invention, the cylindrical single linear slit aerosol concentrator can be combined with a cylindrical radial multi-slit aerosol concentrator. This has specifically the advantage that in a first step a high volume flow can be concentrated by the cylindrical radial multi-slit aerosol concentrator and subsequently a lower volume flow by the cylindrical single linear slit aerosol concentrator. This allows further to operate both concentrators at high efficiencies so that the total efficiency of that two-stage concentration is very high, for instance well over 80%.

Further, according to other aspects of the invention, the system and method may include heliox supplied from one or more heliox sources specifically as a dilution gas, but also as a nozzle gas for aerosolizing the liquid suspension. Apart from a more favorable Reynolds number of heliox allowing for a more laminar flow and therefore for a higher concentrator efficiency, a specific advantage of heliox is its high specific heat and low specific gravity, allowing to enhance the drying process when processing in the evaporation chamber the liquid aerosol to become a dry powder aerosol that may then be concentrated according to preferred embodiments of the invention. Heliox works well for all types of concentrators, specifically here for both a cylindrical single linear slit aerosol concentrator and a cylindrical radial multi-slit aerosol concentrator, but according to the invention works specifically well for a cylindrical single linear slit aerosol concentrator in comparison to air.

DETAILED DESCRIPTION OF THE INVENTION

A fluid to be aerosolized is pumped from a liquid solution or liquid suspension reservoir to a nozzle input end on a nozzle holder where it flows through a central channel to a fluid nozzle. Compressed gas enters the nozzle holder through two gas entrance orifices on the nozzle holder and is transported through at least two gas channels in the nozzle holder to a circumferential pressure equalization chamber and through circumferential converging channels to circumferential diverging channels and finally to an aerosolizing space between the fluid nozzle and a nozzle output end. This configuration is designated a liquid aerosol generating nozzle. The compressed gas may or may not be heated. The details of this nozzle holder and liquid aerosol generating nozzle have been further detailed in patent application U.S. Ser. No. 15/130,235. The liquid solution or liquid suspension to be aerosolized and the compressed gas interact within the aerosolizing space to form a liquid aerosol. This liquid aerosol exits the aerosolizing space through the center of the nozzle output end. A sheath of gas, largely devoid of particles, surrounds the liquid aerosol such that this liquid aerosol does not come in contact with the nozzle output end. In preferred configurations this gas is either air or heliox.

The Weber number, We, provides a measure of how effectively a gas will atomize a liquid.

$$We = \frac{\rho v^2 d}{\sigma}$$

where $\rho$ is the gas density, v is the velocity of the gas, d is a characteristic dimension and $\sigma$ is the surface tension of the liquid. $\rho_{air}$=1.28 kg/m$^3$ $\rho_{heliox}$=0.4 kg/m$^3$. The surface tension for water in contact with air or heliox is similar $\sigma \approx$73 mN/m. We, is 1.62 times higher for heliox than for air and thus heliox is predicted to generate smaller particles at the same gas pressure.

The velocity of gas at the exit of a nozzle can be calculated as:

$$v = \left[\frac{2k}{k-1}RT_0\left(1 - \frac{P^{\frac{k-1}{k}}}{P_0}\right)\right]^{0.5}$$

where k=specific heat ratio, k=1.4 for air, 1.58 for heliox; R=gas constant, R=287 J/kg·K for air, 1546 J/kg·K for heliox; $T_0$=upstream temperature, P=downstream pressure, $P_0$=upstream stagnation pressure. When downstream pressure is P=14.7 psi=1.01×10$^5$ Pa, upstream pressure $P_0$=25 psi=1.72×10$^5$ Pa, upstream gas temperature $T_0$=20° C.=293 K, air velocity at exit of nozzle $v_{air}$=287 m/s, and heliox velocity $v_{heliox}$=661 m/s. Thus, heliox velocity increases 2.3 times. The We for heliox is 1.64 times that for air. As a consequence, for the same driving pressure, heliox generates smaller particles. The very low surface tension of surfactant compared to water leads to a further increase in the Weber number and the effectiveness of its atomization.

The liquid aerosol exiting the nozzle output end forms an aerosol plume that is arrested by a coaxial counter-flow jet of compressed gas exiting a counter flow orifice located about 5 cm from the liquid aerosol generating nozzle. The liquid aerosol so dispersed is transported through a cylindrical evaporation chamber by the flow of preferably warm dry dilution gas that enters the cylindrical evaporation chamber through a flow distributor, surrounding the nozzle holder, which is designed to provide a relatively uniform flow of gas through the cylindrical evaporation chamber. Infrared radiation provided by an infrared source at wavelength within the absorption band for water is transmitted through the walls of the cylindrical evaporation chamber. This infrared radiation together with the warm dry gas causes the water to evaporate from the droplets to form a first intermediate dry powder aerosol. On complete drying, these first intermediate dry aerosols may or may not be solid spherical particles depending largely on the rate of drying and the physicochemical properties of the solution or liquid suspension being aerosolized. Of course if the evaporation of the droplets is incomplete liquid aerosols smaller than the size of the initially generated liquid aerosol will result. In a preferred configuration, the gas is heliox. The specific heat capacity of air is 1.0 kJ/kg·K vs 4.3 kJ/kg·K for heliox. The thermal conductivity of helium is ~6 times higher than air (0.02 vs 0.149 W/m·K). The diffusion coefficients for water vapor are 3.3 times higher in helium compared to air. In addition, convective heat transfer coefficient depends on gas flow around the droplets. The increase in compressed gas flow from the liquid aerosol generating nozzle and thus counter-flow gas velocity increases the rate of water evaporation form the droplets. Thus, given the same compressed gas pressure and nozzle output end diameter, the use of heliox rather than air to generate and process the aerosol reduces the time to evaporate the fluid from the initial droplets resulting in lower losses of particles due to inertial impaction and sedimentation within the processing system. This represents a first configuration of the incident invention. This first intermediate dry powder aerosol may be utilized as it exits the cylindrical evaporation chamber through a cylindrical evaporation chamber output end.

A second configuration of the incident invention comprises an aerosol processing system that includes a liquid aerosol generating nozzle, a counter-flow tube, a flow distributor, a cylindrical evaporation chamber, and a cylindrical linear single slit aerosol concentrator. In this second configuration of the incident invention, the first intermediate dry powder aerosols pass from the cylindrical evaporation chamber output end to the cylindrical linear single slit aerosol concentrator through a cylindrical linear single slit aerosol concentrator input end. The cylindrical linear single slit aerosol concentrator works on the principle of virtual impaction. In this cylindrical linear single slit aerosol concentrator, the velocity of the first intermediate dry powder aerosol entering the cylindrical single slit aerosol concentrator is increased as it passes through a converging cylindrical linear single slit aerosol concentrator input channel. In a preferred configuration, this converging cylindrical linear single slit aerosol concentrator input channel comprises a sculptured channel 3.25 inches long of decreasing cross-sectional area with a circular entrance 70 mm in diameter and a cylindrical linear single slit aerosol concentrator input orifice that in a preferred configuration comprises a slit 32 mm long and 1.3 mm in width and may be between 0.2 and 6 cm long with widths between 1 mm and 2 mm wide. In a preferred configuration, an angle of the walls to the center of the cylindrical linear single slit aerosol concentrator input orifice is 21 degrees, however other angles between 10 and 60 degrees are possible. Aligned with this cylindrical linear single slit aerosol concentrator input orifice and 1.7 mm from it is a cylindrical linear single slit aerosol concentrator output orifice of equal length with a slightly larger width, 1.6 mm, than the cylindrical linear single slit aerosol concentrator input orifice. There is a longitudinal cylindrical linear single slit aerosol concentrator aerosol separation space that in a preferred configuration is of 1.7 mm and preferably between 1 and 2 mm, between the cylindrical linear single slit aerosol concentrator input orifice and cylindrical linear single slit aerosol concentrator output orifice that forms the cylindrical linear single slit aerosol concentrator aerosol separation space and whose magnitude is optimized to diminish any resonance. The cylindrical linear single slit aerosol concentrator output orifice is the entrance of a diverging cylindrical linear single slit aerosol concentrator output channel. The diverging cylindrical linear single slit aerosol concentrator output channel that in a preferred configuration is a sculptured deceleration channel 5 cm long that terminates as a circular exit whose circumference is 35 mm in diameter with other lengths being possible. In a preferred configuration, an angle of the walls to the center of the cylindrical linear single slit aerosol concentrator output orifice is 20 degrees and may be between 10 and 60 degrees. This low angle of divergence minimizes backflow. The first intermediate dry powder aerosol is accelerated as it passes through the converging cylindrical linear single slit aerosol concentrator input channel and exits through the cylindrical linear single slit aerosol concentrator input orifice into the cylindrical linear single slit aerosol concentrator aerosol separation space. The momentum of the first intermediate dry powder aerosol enables most of the aerosols to cross the cylindrical linear single slit aerosol concentrator aerosol separation space and enter the cylindrical linear single slit aerosol concentrator output orifice and into the diverging cylindrical linear single slit aerosol concentrator output channel. A first exhaust aerosol comprising most of the gas, together with a small fraction of the suspended particles, exits the first intermediate dry powder aerosol on each side of the cylindrical linear single slit aerosol concentrator aerosol separation space to enter a sculptured plenum, having a preferred volume of 170 ml with volumes between 30 and 300 ml being possible. An advantage of this configuration is that when the slits of this cylindrical linear single slit aerosol concentrator are vertically aligned, the wall losses in the converging cylindrical linear single slit aerosol concentrator input channel due to gravity are minimal. The first exhaust aerosol that flows through the sculptured plenum has a markedly reduced aerosol concentration compared to the first intermediate dry powder aerosol particle concentration. This sculptured plenum is of sufficient volume that this first exhaust aerosol containing a fraction of the particles entering the cylindrical linear single slit aerosol concentrator does not substantially interfere with the flow of the first intermediate aerosol crossing the cylindrical linear single slit aerosol concentrator aerosol separation space. The first exhaust aerosol exits the sculptured plenum through a cylindrical linear single slit aerosol concentrator exhaust port that in a preferred configuration is 15 mm in diameter. This port size suppresses the formation of any resonant standing waves within the sculptured plenum.

The impaction parameter for an aerosol is:

$$\phi = \frac{C\rho_p d_p^2 v}{18\mu D_j}$$

where $\phi$=impaction parameter, dimensionless; C=Cunningham correction for particles with sizes comparable to the mean free path of the gas molecules; $\rho_p$=specific gravity of particles, g/cm$^3$; $d_p$=diameter of particles, cm; v=velocity of jet, cm/sec; $D_j$ is diameter of jet, cm; $\mu$=viscosity of gas, Pa·s; viscosities of heliox and air are similar, $\mu_{air}$=18×10$^{-6}$ Pa·s and $\mu_{heliox}$=19.1×10$^{-6}$ Pa·s. The relative Reynolds numbers for air is 3.2 times that of heliox. Enabling the cylindrical linear single slit aerosol concentrator to operate at high heliox flow rates with low pressure differentials across the cylindrical linear single slit aerosol concentrator as well as between the cylindrical evaporation chamber and the first exhaust aerosol. A respirable dry powder aerosol exiting the diverging cylindrical linear single slit aerosol concentrator output channel has a small positive pressure with its respirable dry powder aerosol volume flow being limited by an aerosol receiving device connected to the diverging cylindrical linear single slit aerosol concentrator output channel. The respirable dry powder aerosol may be outputted by connecting to the diverging cylindrical linear single slit aerosol concentrator output to a cylindrical linear single slit aerosol concentrator collection cone, a filter, an apparatus or inhaled by a mammal.

In a third configuration of the incident invention a cylindrical radial multi-slit aerosol concentrator is attached to the cylindrical evaporation chamber output end such that the first intermediate dry powder aerosol through the cylindrical evaporation chamber output end enters a cylindrical radial multi-slit aerosol concentrator input end. The essential features of this cylindrical radial multi-slit aerosol concentrator have been previously described, U.S. Pat. No. 8,375,987 and are herein incorporated in their entirety. It has 16 acceleration slit orifices. In this configuration, the first intermediate dry powder aerosol is transported from the cylindrical evaporation chamber output end to the cylindrical radial multi-slit concentrator input end and thence to radially aligned acceleration nozzles where the aerosol is accelerated. The particles contained in the first intermediate dry powder aerosol cross a cylindrical radial multi-slit aerosol concentrator aerosol separation space between acceleration slit orifices and deceleration slit orifices and enter radially aligned deceleration nozzles where a first intermediate dry powder aerosol volume flow is reduced to form a second intermediate dry powder aerosol. A second exhaust aerosol containing gas and a small percentage of the particles exit through the cylindrical radial multi-slit aerosol concentrator aerosol separation space between the acceleration slit orifices and deceleration slit orifices and into a circular plenum to be exhausted through cylindrical radial multi-slit aerosol concentrator exhaust ports on the wall of the circular plenum. A second intermediate dry powder aerosol volume flow is controlled by an external device connected to a cylindrical radial multi-slit concentrator output end through which the second intermediate dry powder aerosol is outputted.

In a fourth configuration of the incident invention, the cylindrical linear single slit aerosol concentrator input end of the cylindrical linear single slit aerosol concentrator is connected to the cylindrical radial multi-slit aerosol concentrator output end. When the cylindrical radial multi-slit aerosol concentrator and the cylindrical linear single slit aerosol concentrator are connected they comprise a two-stage concentrator. In a preferred configuration the combined slit length of the slits of the cylindrical radial multi-slit aerosol concentrator is 141 mm whereas the cylindrical linear single slit aerosol concentrator has a slit length of 32 mm making a ratio of 4.4 to 1, with ratios between 2 to 1 and 6 to one being possible. The widths of the cylindrical linear single slit aerosol concentrator input orifice and acceleration slit orifices of the cylindrical radial multi-slit aerosol concentrator are similar as are the widths of the cylindrical linear single slit aerosol concentrator output orifice and the deceleration slit orifices of the cylindrical radial multi-slit aerosol concentrator as is the cylindrical linear single slit aerosol concentrator aerosol separation space compared to the cylindrical radial multi-slit aerosol concentrator aerosol separation space. Given this configuration, when the respirable dry powder aerosol volume flow of the second stage, cylindrical linear single slit aerosol concentrator, is set, the distribution of aerosol volume flow through each of the stages and their relative exhaust ports is such that the ratio of the input/output flow of each concentrator is much less than a single concentrator with a much higher input/output ratio.

In this fourth configuration, the second intermediate aerosol exiting the radially aligned deceleration nozzles enters the converging cylindrical linear single slit aerosol concentrator input channel where the second intermediate aerosol is accelerated through the converging cylindrical linear single slit aerosol concentrator input channel towards the cylindrical linear single slit aerosol concentrator input orifice. As previously described, most of the particles exiting the cylindrical linear single slit aerosol concentrator input orifice cross the cylindrical linear single slit aerosol concentrator aerosol separation space and enter through the cylindrical linear single slit concentrator output orifice to the diverging cylindrical linear single slit aerosol concentrator output channel whereas the first exhaust aerosol exits the cylindrical linear single slit aerosol concentrator aerosol separation space and flows into and through the sculptured plenum to the cylindrical linear single slit aerosol concentrator exhaust port in the outer wall of the sculptured plenum. The respirable dry powder aerosol volume flow exiting the diverging cylindrical linear single slit aerosol concentrator output channel is controlled external to the cylindrical linear single slit aerosol concentrator and comprises the respirable dry powder aerosol.

The advantage of the two-stage configuration is that the ratio of the aerosol volume flow entering to that exiting each stage is less than when only the cylindrical radial multi-slit concentrator is used at a considerably higher input to output volume flow ratio. The efficiency of using a two-stage concentrator is higher than using a one-stage cylindrical radial multi-slit aerosol concentrator and that the pressure at the second stage output end is extremely low. These features increase the utility and flexibility of this configuration.

The cylindrical linear single slit aerosol concentrator can be used a) for heliox, b) for low volume air applications where low outputs are desirable such as when delivering aerosols to infants, children and animals, and c) as a component of a two-stage concentrator when connected in series with the present cylindrical radial multi-slit concentrator.

DETAILED DESCRIPTION OF THE DRAWINGS

Figure 1A:
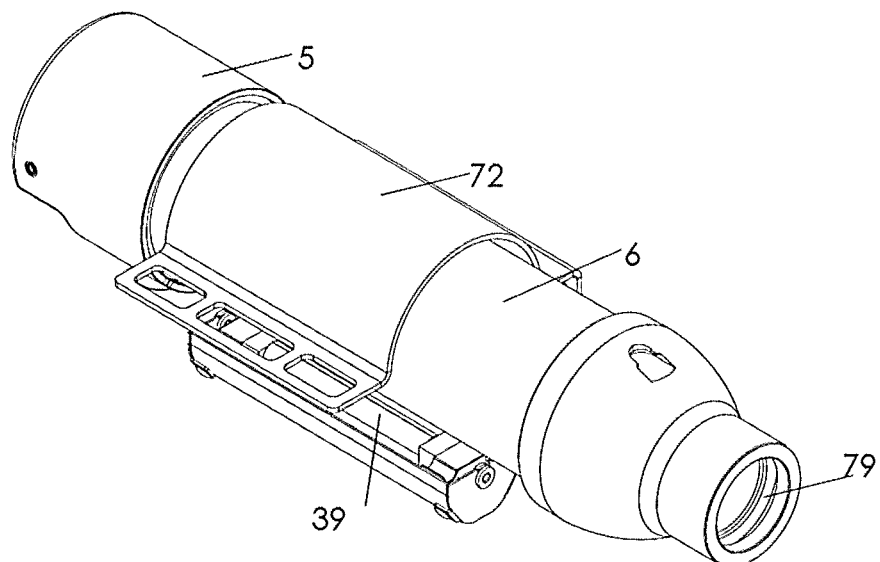
FIG. 1A shows perspective view of an aerosol generating system according to an embodiment of the invention.
Figure 1B:
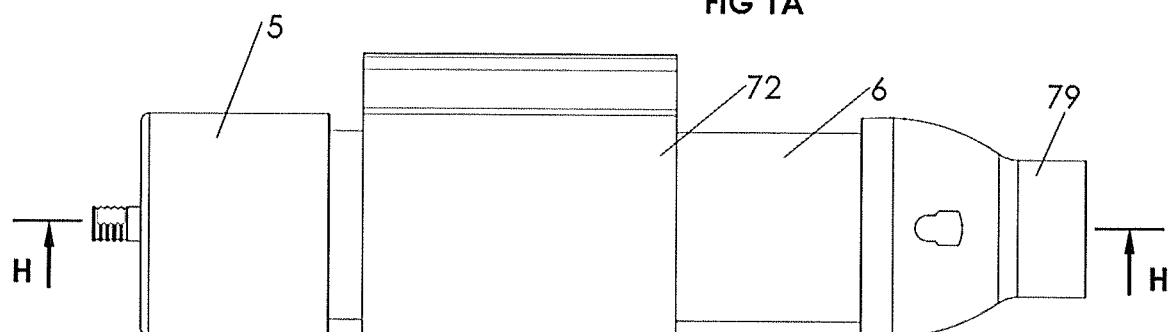
FIG. 1B shows a top view of the embodiment shown in FIG. 1A.
Figure 1C:
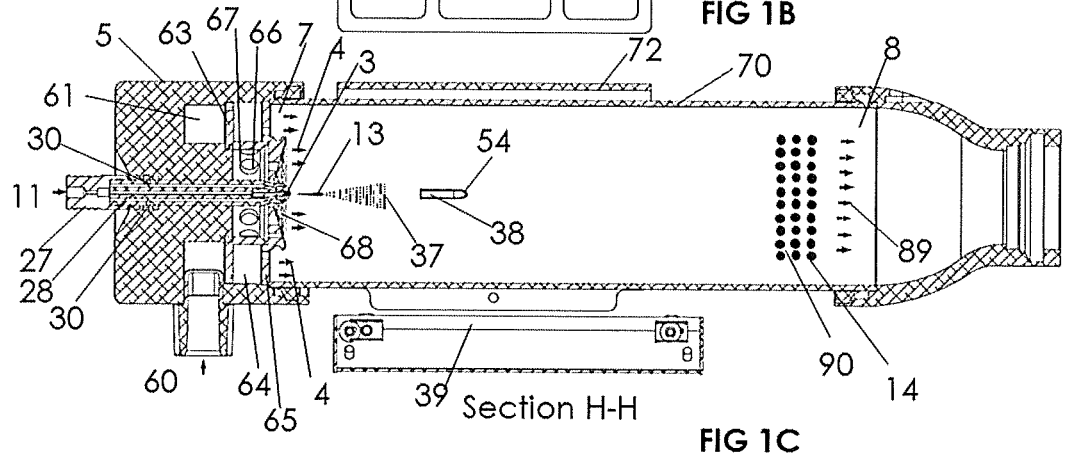
FIG. 1C shows a longitudinal section denoted H-H in FIG. 1B.
Figure 3A:
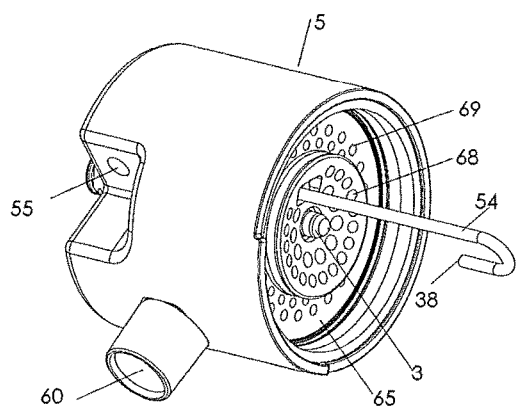
FIG. 3A shows a perspective view of a liquid aerosol generating nozzle and a flow distributor subassembly as included in the embodiments of the invention.
Figure 3B:
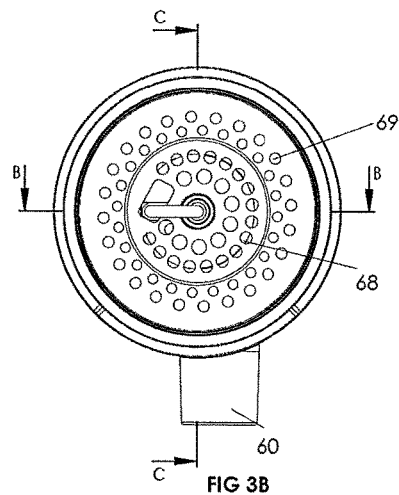
FIG. 3B shows a front view of the subassembly as shown in FIG. 3A.
Figure 3C:
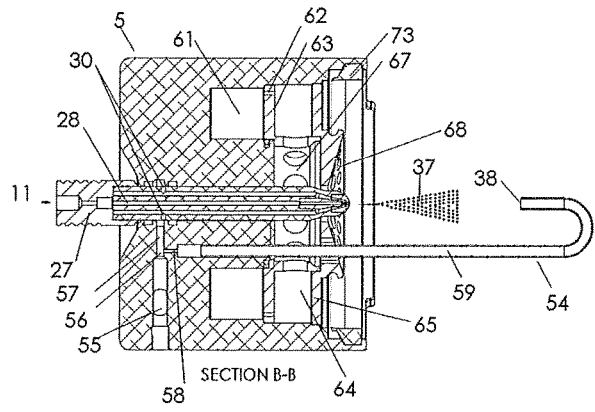
FIG. 3C shows a longitudinal section denoted B-B in FIG. 3B.
Figure 3D:
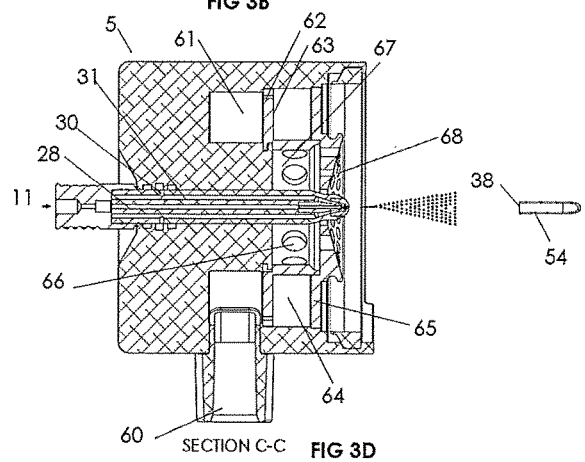
FIG. 3D shows a longitudinal section denoted C-C in FIG. 3B.
Figure 4A:
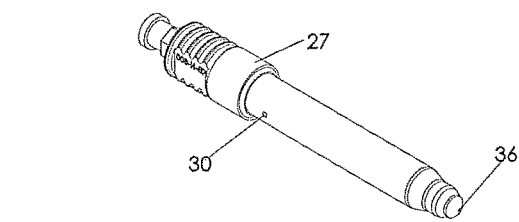
FIG. 4A shows a perspective view of a liquid aerosol generating nozzle and a nozzle subassembly included in the embodiments of the invention.
Figure 4C:
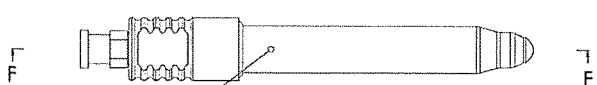
FIG. 4C shows a side view of the subassembly shown in FIG. 4A.
Figure 4D:
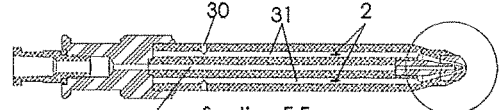
FIG. 4D shows longitudinal section denoted F-F in FIG. 4C.
Figure 4B:
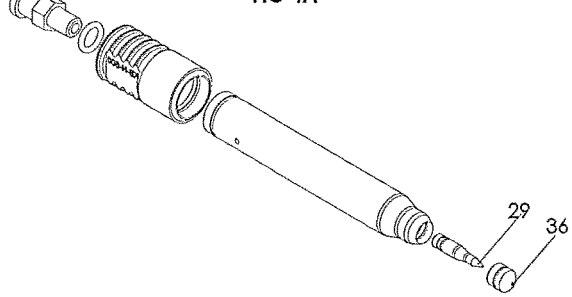
FIG. 4B shows an exploded perspective view of the subassembly shown in FIG. 4A.
Figure 4E:
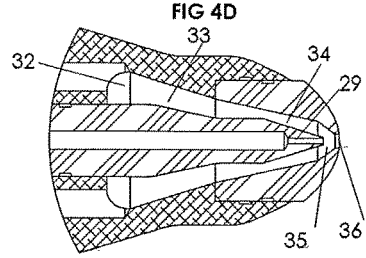
FIG. 4E shows detailed structure denoted A in FIG. 4D.

A first configuration of the incident invention comprises an aerosol generating system that includes a liquid aerosol generating nozzle 3, a counter-flow tube 54, a flow distributor 5, and a cylindrical evaporation chamber 6 is shown in FIG. 1. The liquid aerosol generating nozzle 3 is described in detail in U.S. patent application Ser. No. 15/130,235. The flow distributor 5 and the cylindrical evaporation chamber 6 are described in U.S. Pat. No. 8,616,532. This application and patent, respectively, are hereby by incorporated by reference into this application in their entirety. A perspective and a cross-sectional view of the liquid aerosol generating nozzle 3 are shown in FIG. 4. The flow distributor 5 is shown in FIG. 3. A fluid to be aerosolized is fed under pressure into a nozzle input end 11 of a nozzle holder 27, FIG. 1C. This fluid flows from the nozzle input end 11 through a central channel 28 in the nozzle holder 27 to a fluid nozzle 29 and then to an aerosolizing space 35 as depicted in FIG. 4E. Compressed gas, that may or may not be heated, is provided through a nozzle gas supply 55 in the flow distributor 5 (FIG. 3A). This compressed gas flows from the nozzle gas supply 55 in the flow distributor 5, to a channel 56 where the flow is split (FIG. 3C). One portion flows through a compressed gas channel 57 that connects to two compressed gas entrance orifices 30 on the nozzle holder 27 (FIG. 4D). As shown in FIGS. 3C and 4D, the gas in the form of a nozzle gas 2 flows from these gas entrance orifices 30 through gas channels 31 (FIG. 4D) into a circumferential pressure equalization chamber 32 as shown in FIG. 4E. The nozzle gas 2 flows from this circumferential pressure equalization chamber 32 through to a circumferential converging channel 33 to a circumferential diverging channel 34 to the aerosolizing space 35 where it interacts with the fluid entering the aerosolizing space 35. An ensuing liquid aerosol 13 exits the aerosolizing space 35 through a nozzle output end 36 (FIG. 4E) and forms an aerosol plume 37 as shown in FIGS. 1C and 3C. As shown in FIG. 3C, another portion of the gas flow passes through a constriction orifice 58 and through a counter flow channel 59 to a counter flow orifice 38 that is coaxial with the central channel 28. This gas forms a jet that is of opposite direction and coaxial with the aerosol plume 37 of the liquid aerosol 13. This jet arrests the aerosol plume 37 of the liquid aerosol 13. This counter flow gas could be provided and its flow regulated independently of the compressed gas to the liquid aerosol generating nozzle 3. As shown in FIGS. 3A and 3D, dilution gas 4, that may or may not be heated, enters a dilution gas supply 60 in the flow distributor 5, from which it flows into a donut shaped chamber 61 and through holes 62 in a first baffle 63 to a second circular chamber 64 and again through a second baffle 65 into the cylindrical evaporation chamber 6 (FIG. 1C). Some of the gas that enters the second circular chamber 64 flows through holes 66 in an inner cylindrical chamber 67 and from there flows through central holes 68 in the central region of a second baffle 65 into the cylindrical evaporation chamber 6. The dilution gas 4 flows through both central and peripheral holes, 68 and 69 (see FIGS. 3A and 3B), in the second baffle 65 into the cylindrical evaporation chamber 6 carrying with it the arrested aerosol plume 37 and transports this liquid aerosol 13 through the cylindrical evaporation chamber 6. This cylindrical evaporation chamber 6 in a preferred configuration is comprised of a quartz tube 70 23 cm long with a 7 cm outside diameter (FIG. 1C), however other lengths and diameters are possible. Infrared radiation from an infrared source 39 (FIGS. 1A and 1C) adjacent to the cylindrical evaporation chamber 6, is transmitted through walls of the quartz tube 70. A reflector 72 on the opposite side of the cylindrical evaporation chamber 6 to the infrared source 39, reflects the infrared radiation transmitted through the opposing wall of the quartz tube 70 back into the cylindrical evaporation chamber 6. The reflector 72 is made out of aluminum with the shape of half cylinder, however other materials and shapes are possible. As the liquid aerosol 13 is diluted by the dilution gas 4 and passes through this radiant field, the water in the droplets is rapidly evaporated forming a first intermediate dry powder aerosol 14. The resultant solid phase first intermediate dry powder aerosol 14 exits from a cylindrical evaporation chamber output end 8 where it can be utilized.

Figures 2A, 2B, 2C:
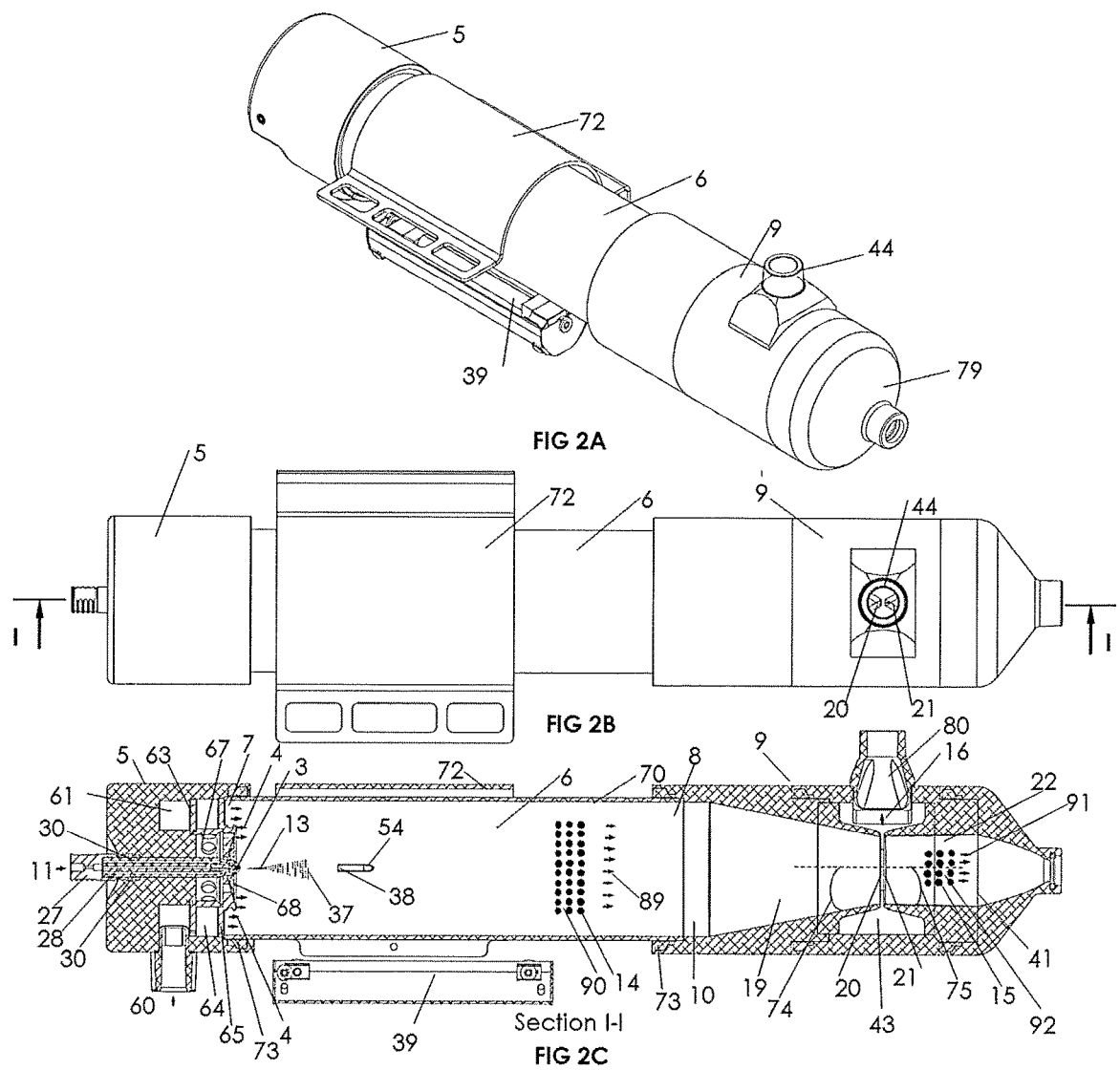
FIG. 2A shows a perspective view of an aerosol generating system according to an embodiment of the invention including a cylindrical single linear slit aerosol concentrator.
FIG. 2B shows a top view of the of the embodiment shown in FIG. 2A.
FIG. 2C shows a longitudinal section denoted I-I in FIG. 2B.
Figure 5A:
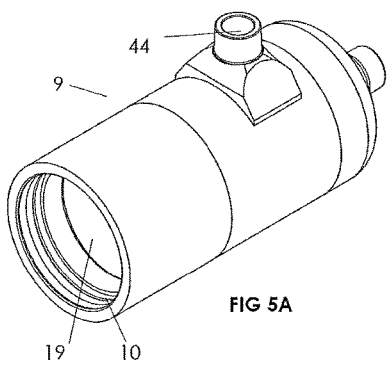
FIG. 5A shows a perspective view of a cylindrical single linear slit aerosol concentrator subassembly included in the embodiments of the invention.
Figure 5C:
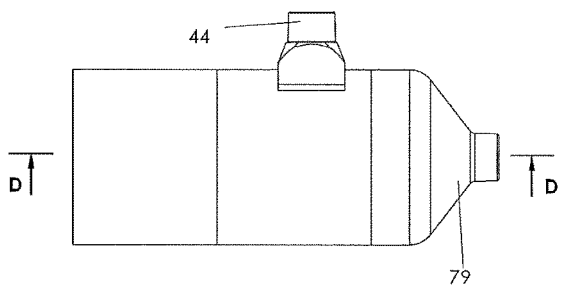
FIG. 5C shows a side view of the subassembly shown in FIG. 5A.
Figure 5B:
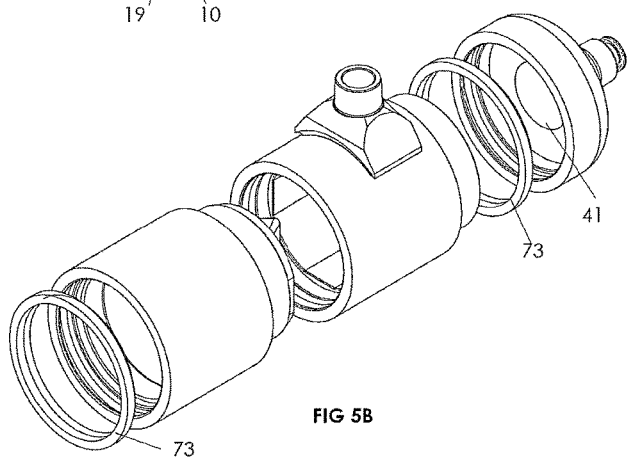
FIG. 5B shows an exploded perspective view of the subassembly shown in FIG. 5A.
Figure 5D:
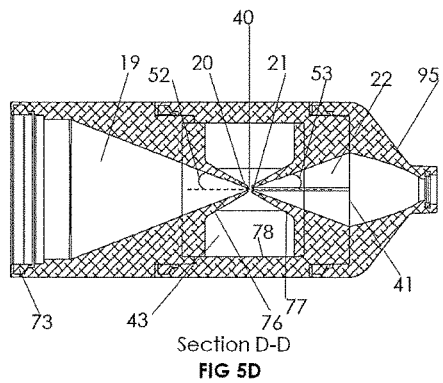
FIG. 5D shows longitudinal section denoted D-D in FIG. 5C.

A second configuration of the incident invention comprises an aerosol generating system that includes the liquid aerosol generating nozzle 3, the counter-flow tube 54, the flow distributor 5, the cylindrical evaporation chamber 6, and a cylindrical single linear slit aerosol concentrator 9, is shown in FIGS. 2A-2C. In this configuration, the resultant solid phase first intermediate dry powder aerosol 14 exits from the cylindrical evaporation chamber 6 into the cylindrical single linear slit aerosol concentrator 9 that is connected to the cylindrical evaporation chamber output end 8. The connections of a cylindrical evaporation chamber input end 7 to the flow distributor 5 and the cylindrical evaporation chamber output end 8 to a cylindrical single linear slit aerosol concentrator input end 10 are made gas tight by the use of lip-seals 73. This cylindrical single linear slit aerosol concentrator 9 is comprised of a converging cylindrical single linear slit aerosol concentrator input channel 19 (FIG. 5A-5D), 8.4 cm long is sculptured such that the end of this channel is a cylindrical single linear slit aerosol concentrator input orifice 20 that comprises a slit 33 mm long and 1 mm wide. A converging cylindrical single linear slit aerosol concentrator input orifice angle 74 (FIG. 2C) and a converging cylindrical single linear slit aerosol concentrator input channel angle 52 (FIG. 5D) of the walls are 11° to the ends of a cylindrical single linear slit aerosol concentrator input orifice 20 and 21° to the center of the cylindrical single linear slit aerosol concentrator input orifice 20. A cylindrical single linear slit aerosol concentrator output orifice 21 34-mm-long and 1.4-mm-wide diverges to a circular exit 41 so forming a diverging cylindrical single linear slit aerosol concentrator output channel 22. A diverging cylindrical single linear slit aerosol concentrator output orifice angle 75 and a diverging cylindrical single linear slit aerosol concentrator output channel angle 53 of the walls of the diverging cylindrical single linear slit aerosol concentrator output channel 22 are 1.4° to the ends of the cylindrical single linear slit aerosol concentrator output orifice 21 and 20.3° to the center of the cylindrical single linear slit aerosol concentrator output orifice 21. The diverging cylindrical single linear slit aerosol concentrator output channel 22 together with the cylindrical single linear slit aerosol concentrator output orifice 21 are positioned such that they are precisely aligned with the converging cylindrical single linear slit aerosol concentrator input channel 19 and the cylindrical single linear slit aerosol concentrator input orifice 20. There is a cylindrical single linear slit aerosol concentrator aerosol separation space 40 1.7 mm between the cylindrical single linear slit aerosol concentrator input orifice 20 and the cylindrical single linear slit aerosol concentrator output orifice 21. There is a sculptured plenum 43 formed by an external surface 76 of the end portions of the converging cylindrical single linear slit aerosol concentrator input channel 19 and an external surface 77 of the diverging cylindrical single linear slit aerosol concentrator output channel 22 and an internal wall 78 of the cylindrical single linear slit aerosol concentrator 9. This sculptured plenum 43 has a cylindrical single linear slit aerosol concentrator exhaust port 44 aligned with the longitudinal axis of the cylindrical single linear slit aerosol concentrator input and output orifices, 20 and 21. This cylindrical single linear slit aerosol concentrator exhaust port 44 has an internal diameter of 15 mm. The first intermediate dry powder aerosol 14 at a first intermediate dry powder aerosol volume flow 89 and a first intermediate dry powder aerosol particle concentration 90 is accelerated as it flows through the converging cylindrical single linear slit aerosol concentrator input channel 19 to and through the cylindrical single linear slit aerosol concentrator input orifice 20. The momentum of the particles exiting the cylindrical single linear slit aerosol concentrator input orifice 20 enables most of the particles comprising the first intermediate aerosol 14 to cross the cylindrical single linear slit aerosol concentrator aerosol separation space 40 and enter the cylindrical single linear slit aerosol concentrator output orifice 21 to form a respirable dry powder aerosol 15. A small fraction of the first intermediate dry powder aerosol 14 exits the first intermediate dry powder aerosol 14 through the cylindrical single linear slit aerosol concentrator aerosol separation space 40 into the sculptured plenum 43 at a right angle to the first intermediate dry powder aerosol volume flow 89 direction to form a first exhaust aerosol 16. The first exhaust aerosol 16 flows through the sculptured plenum 43 to exit a sculptured exhaust channel 80 (FIG. 2C) to the cylindrical single linear slit aerosol concentrator exhaust port 44. The respirable dry powder aerosol 15 at a respirable dry powder aerosol volume flow 91 and a respirable dry powder aerosol particle concentration 92 flows through the diverging cylindrical single linear slit aerosol concentrator output channel 22 to a collection cone 79. A device connected to this collection cone 79 controls the respirable dry powder aerosol volume flow 91 of the respirable dry powder aerosol 15.

Figure 6A:
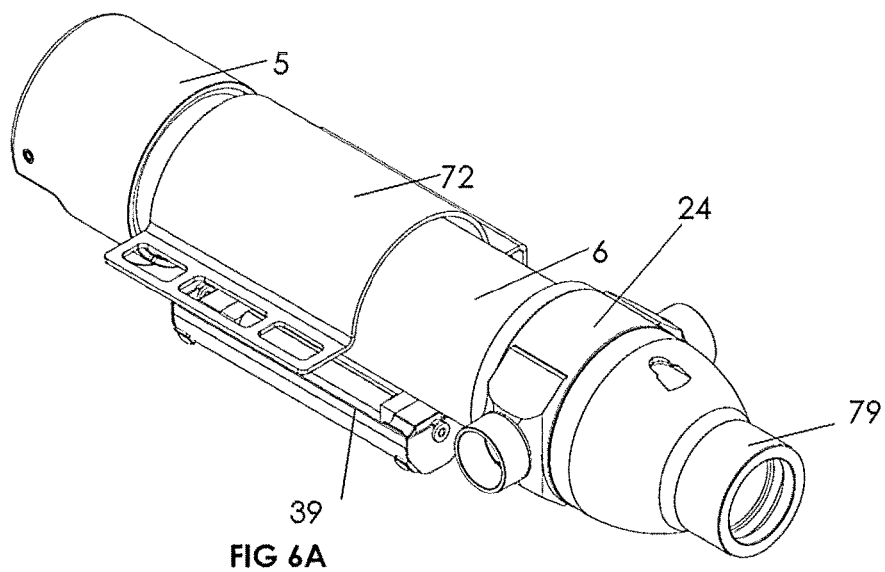
FIG. 6A shows a perspective view of an aerosol generating system according to an embodiment of the invention including a cylindrical radial multi-slit aerosol concentrator.
Figure 6B:
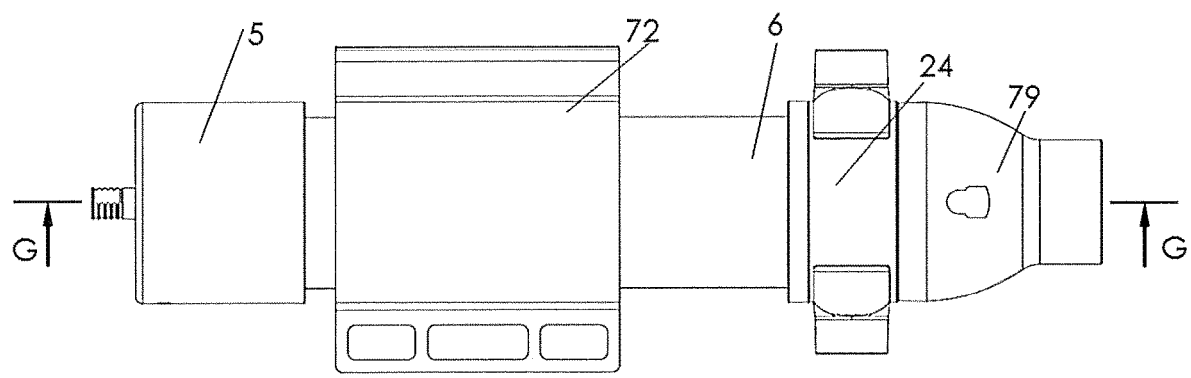
FIG. 6B shows a top view of the embodiment shown in FIG. 6A.
Figure 6C:
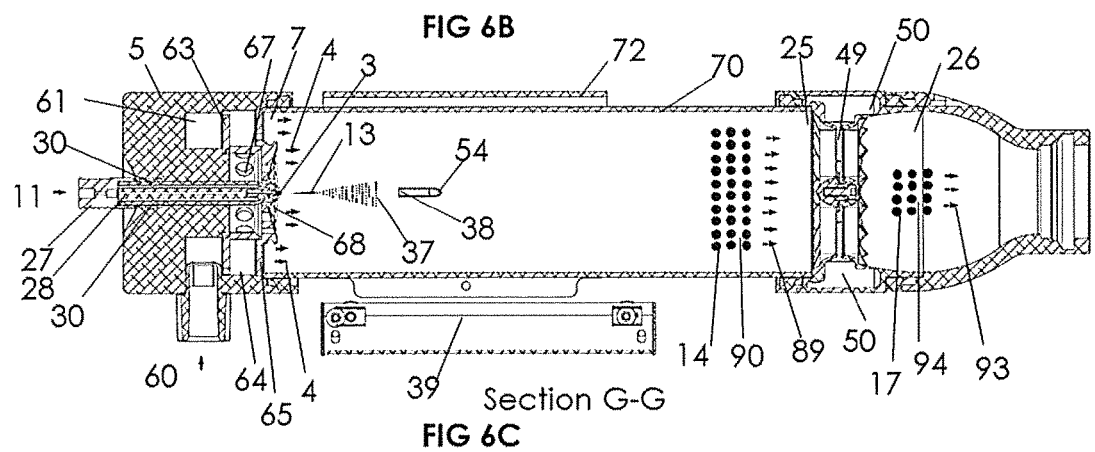
FIG. 6C shows a longitudinal section denoted G-G in FIG. 6B.
Figure 7A:
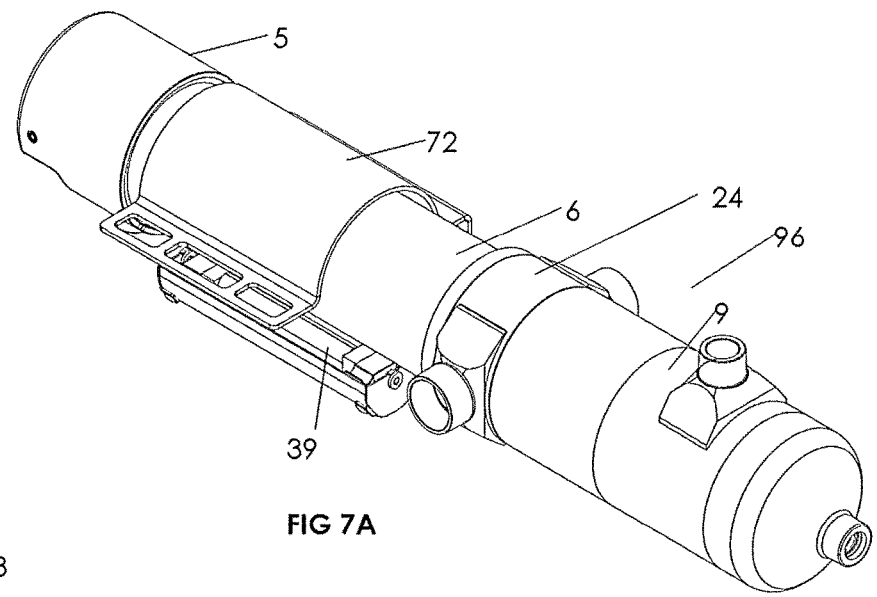
FIG. 7A shows a perspective view of an aerosol generating system according to an embodiment of the invention including both a cylindrical radial multi-slit and a cylindrical single linear slit aerosol concentrators in series.
Figure 7B:
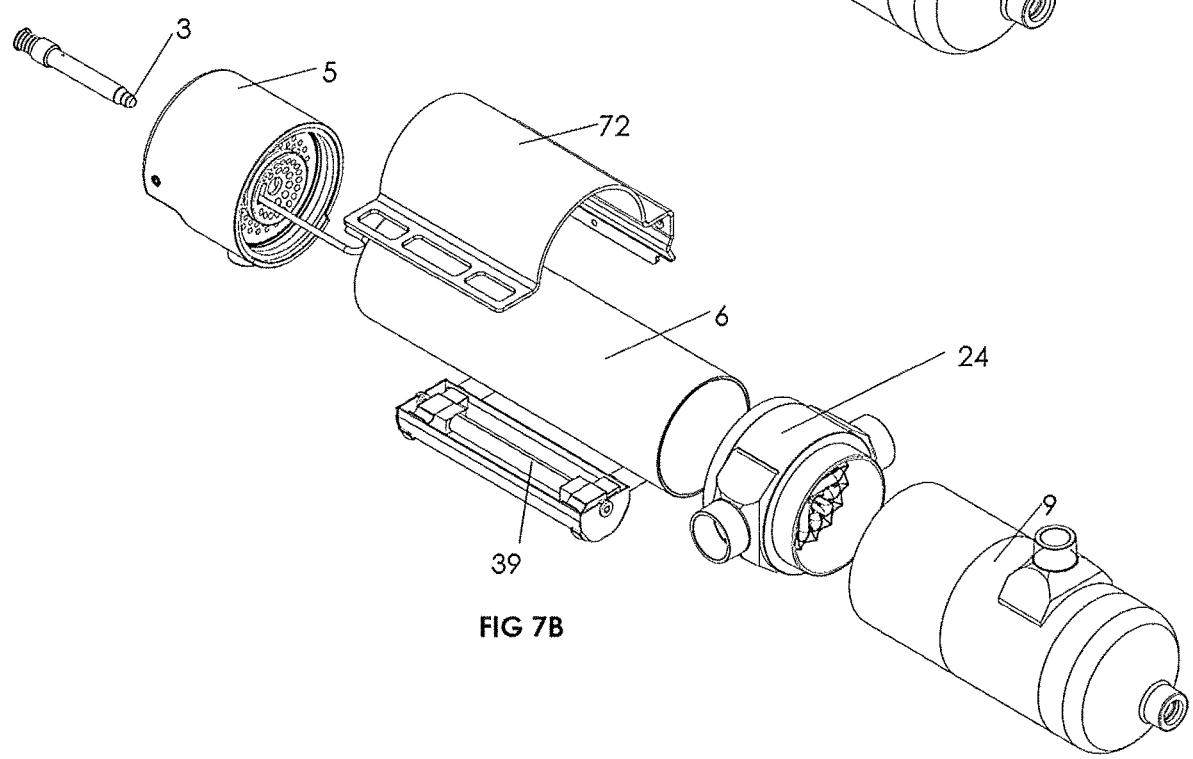
FIG. 7B shows an exploded perspective view of the aerosol generating system shown in FIG. 7A.
Figure 7C:
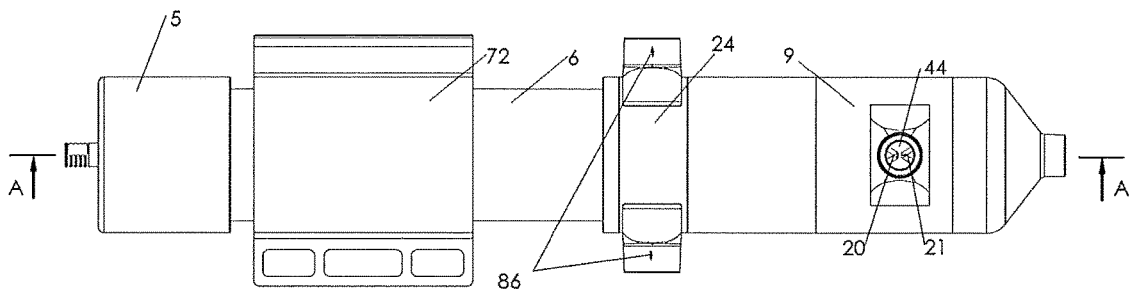
FIG. 7C shows a top view of the aerosol processing system of the aerosol generating system shown in FIG. 7A.
Figure 7D:
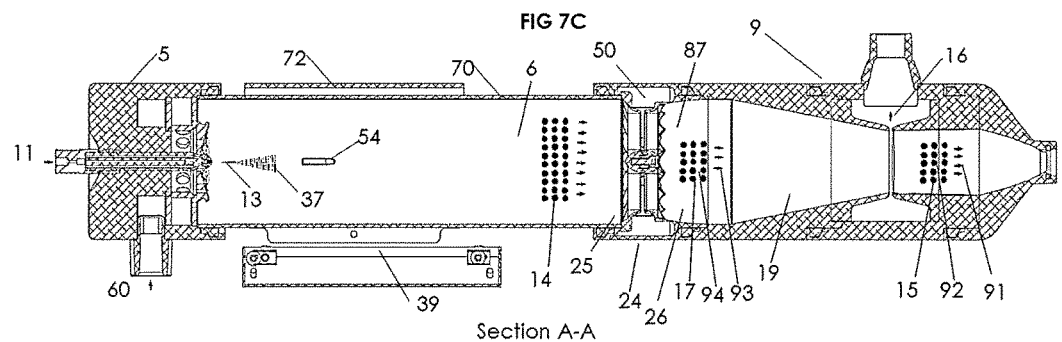
FIG. 7D shows a longitudinal section denoted A-A in FIG. 7C.
Figure 8A:
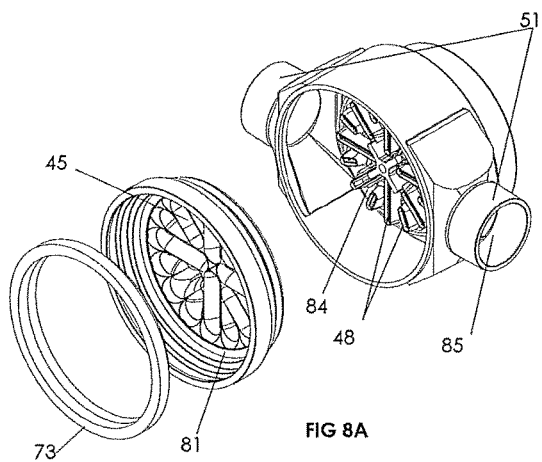
FIG. 8A shows an exploded front perspective view of a cylindrical radial multi-slit aerosol concentrator.
Figure 8B:
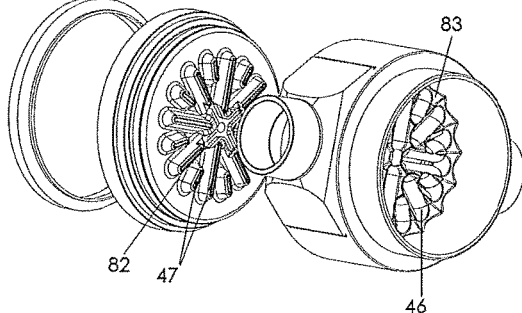
FIG. 8B shows an exploded rear perspective view of the cylindrical radial multi-slit aerosol concentrator shown in FIG. 8A.
Figure 8C:
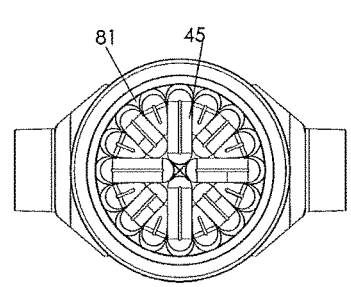
FIG. 8C shows a front view of the cylindrical radial multi-slit aerosol concentrator shown in FIG. 8A.
Figure 8D:
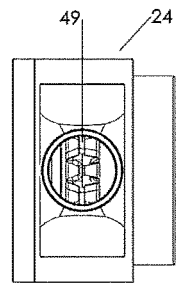
FIG. 8D shows a side view of the cylindrical radial multi-slit aerosol concentrator shown in FIG. 8A.
Figure 8E:
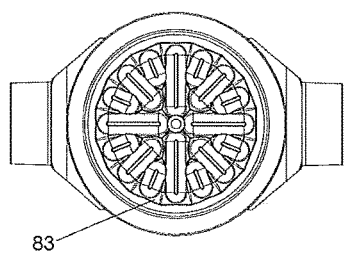
FIG. 8E shows a back view of the cylindrical radial multi-slit aerosol concentrator shown in FIG. 8A.

A third configuration of the incident invention comprises an aerosol generating system that includes the liquid aerosol generating nozzle 3, the counter-flow tube 54, the flow distributor 5, the cylindrical evaporation chamber 6, and a cylindrical radial multi-slit aerosol concentrator 24 that are connected as shown in FIG. 6A-6C. A similar cylindrical radial multi-slit aerosol concentrator 24 has been described in U.S. Pat. No. 8,375,987 and is hereby incorporated in its entirety. In this third configuration the cylindrical evaporation chamber output end 8 is connected to a cylindrical radial multi-slit aerosol concentrator input end 25. The configuration of the cylindrical radial multi-slit aerosol concentrator 24 is shown in FIG. 8A-8E. An entrance plate 81 has 16 radially aligned acceleration nozzles 45 with the longer of these nozzles extending towards the center and with shorter of these nozzles located more towards the periphery. The radially aligned acceleration nozzles 45 are aerodynamically sculptured to reduce aerosol deposition. At the narrow end of these radially aligned acceleration nozzles 45 are acceleration slit orifices 47. These acceleration slit orifices 47 have a width of 1 mm. On the other side of the entrance plate 81 the radially aligned acceleration nozzles 45 protrude to form entrance plate channels 82 that are contiguous with a circular plenum 50 (FIG. 6C). Aligned with these radially aligned acceleration nozzles 45 but opposite in direction is a corresponding rear plate 83 with set of similarly sculptured radially aligned deceleration nozzles 46. Again these radially aligned deceleration nozzles 46 protrude to form rear plate channels 84 that are contiguous with the entrance plate channels 82 and the circular plenum 50. These radially aligned deceleration nozzles 46 have deceleration orifices 48 width of 1.4 mm. The radially aligned acceleration nozzles 45 are separated from the radially aligned deceleration nozzles 46 by a cylindrical radial multi-slit aerosol concentrator aerosol separation space 49 of 1.8 mm. The circular plenum 50 is contiguous with two converging exhaust channels 85 on opposite sides of the cylindrical radial multi-slit aerosol concentrator 24 that terminate in cylindrical radial multi-slit aerosol concentrator exhaust ports 51 with medical fitting tapers to facilitate the securing of filters on these cylindrical radial multi-slit aerosol concentrator exhaust ports 51. In this configuration, the first intermediate dry powder aerosol 14 transported through the cylindrical evaporation chamber 6 enters the radially aligned acceleration nozzles 45 with a resultant increase in velocity such that the particles in the first intermediate dry powder aerosol 14 have the momentum to cross the cylindrical radial multi-slit aerosol concentrator aerosol separation space 49 between the acceleration slit orifices 47 and deceleration slit orifices 48 and enter the radially aligned deceleration nozzles 46 as a second intermediate dry powder aerosol 17. A fraction of the aerosol exits through the cylindrical radial multi-slit aerosol concentrator aerosol separation space 49 at right angles to the first intermediate dry powder aerosol 14 flow to form a second exhaust aerosol 86. The second exhaust aerosol 86 flows through the entrance plate and rear plate channels 82 and 84 to the circular plenum 50 where it flows to the two converging exhaust channels 85 and then exits through the cylindrical radial multi-slit aerosol concentrator exhaust ports 51. The first intermediate dry powder aerosol 14 decreases in velocity as it passes through the radially aligned deceleration nozzles 46 to form the second intermediate dry powder aerosol 17 at a second intermediate dry powder aerosol volume flow 93 and a second intermediate dry powder aerosol particle concentration 94 which in turn flows through a cylindrical radial multi-slit aerosol concentrator output end 26 (FIG. 6C). The second intermediate dry powder aerosol volume flow 93 is controlled by an output device connected to the collection cone 79.

A fourth configuration the incident invention is an aerosol generating system that comprises the liquid aerosol generating nozzle 3, the counter-flow tube 54, the flow distributor 5, the cylindrical evaporation chamber 6, and a two-stage concentrator 96 that includes the cylindrical radial multi-slit aerosol concentrator 24, and the cylindrical single linear slit aerosol concentrator 9 is shown in FIG. 7A-7D. In this configuration, the second intermediate dry power aerosol 17 flows from the cylindrical radial multi-slit concentrator output end 26 into the converging cylindrical single linear slit aerosol concentrator input channel 19 of the cylindrical single linear slit aerosol concentrator 9. This second intermediate dry powder aerosol 17 is processed by the cylindrical single linear slit aerosol concentrator 9 in a similar manner as the first intermediate dry powder aerosol 14 in the second configuration is processed by this cylindrical single linear slit aerosol concentrator 9. The respirable dry powder aerosol 15 flows through the diverging cylindrical single linear slit aerosol concentrator output channel 22 to the collection cone 79. A device connected to this cone controls respirable dry powder aerosol volume flow 91 of the respirable dry powder aerosol 15. In this two-stage configuration, the flow distribution throughout this two-stage concentrator 96 is governed by controlling the respirable dry powder aerosol volume flow 91 of the cylindrical single linear slit aerosol concentrator 9.

EXAMPLES

The following data were generated using the incident invention operated with the aerosol processing system aligned horizontally atop its control console.

To evaluate the performance of the incident invention, various concentrations of polyvinylpyrridolidone (PVP), a polymeric excipient that can be obtained in a wide range of molecular weights were used. PVP was used both as a surrogate for surfactant and other medications which form solutions or suspensions within the range of viscosities studied. Surfactant suspensions provided by Molecular Express were used that comprise the phospholipids contained in Minisurf. The particle size was measured with a Maple-Miller cascade impactor and expressed as mass median aerodynamic diameter, MMAD. The heliox used in these experiments was 80% helium and 20% oxygen.

The effects on particle size of aerosol generation and processing with heliox compared to air were evaluated in the third configuration of the incident invention where the cylindrical radial multi-slit aerosol concentrator was incorporated in the incident invention.

Figure 9:
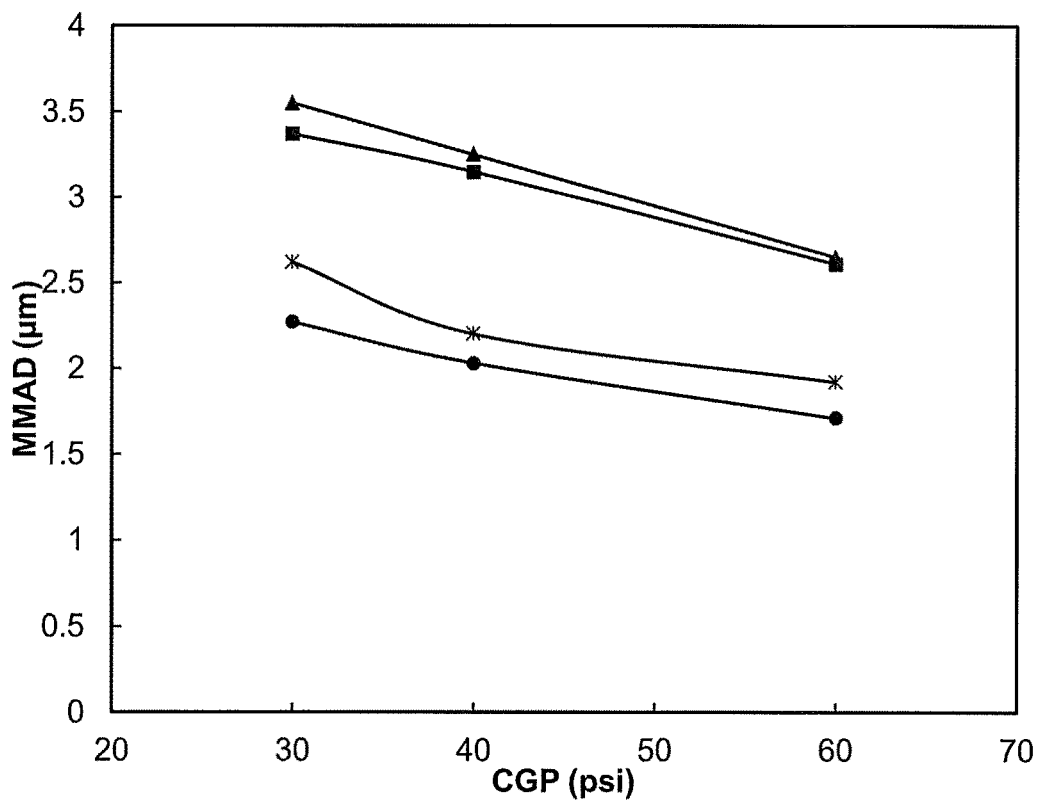
FIG. 9 shows a diagram demonstrating the influence of the compressed gas pressure (CGP) on the mass median aerodynamic diameter (MMAD) of the aerosol particles in μm for PVP solutions by using a cylindrical radial multi-slit aerosol concentrator. The triangular, circular-, square, and astroid dots denote the aerosols generated by the nozzles KB-N-500 (air), KB-N-500 (heliox), KB-N-600 (air), and KB-N-600 (heliox), respectively.

To evaluate the effects of gas pressure particles were generated with nozzles KB-N-500 and KB-N-600 using 10% 8 kDa PVP at 1 ml/min. The first intermediate dry powder aerosol volume flow were in the range of 160-200 l/min. Additionally, the respirable dry powder aerosol volume flow was controlled as 30 l/min. There was a marked reduction in MMAD of the output of the incident invention using the radial-slit concentrator when heliox is used compared to air as the aerosol generating and processing gas (FIG. 9, 10). The particle size decreased with increasing compressed gas pressure (CGP) (FIG. 9).

Figure 10:
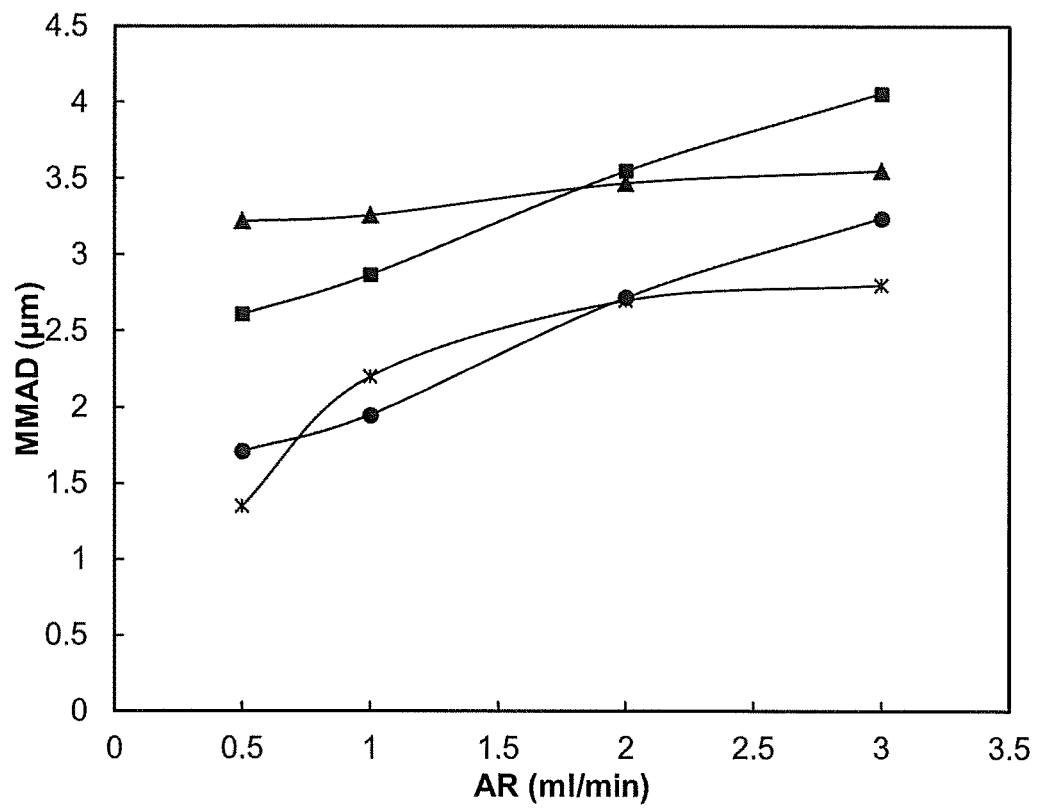
FIG. 10 shows a diagram demonstrating the influence of the aerosolization rate (AR) of the fluid to be aerosolized in ml/min on the mass median aerodynamic diameter (MMAD) of the aerosol particles in μm for both PVP solutions and surfactant suspensions. The square, triangular, circular, and astroid dots denote the aerosols generated from 10% 8 kDa PVP (air), 9.33% surfactant (air), 10% 8 kDa PVP (heliox), and 9.33% surfactant (heliox), respectively.

To evaluate the effects of aerosolization rate on particle size with air and heliox aerosols generated from 9.33% surfactant suspensions and 10% 8 kDa PVP solutions using nozzle KB-N-500 at compressed air/heliox pressure of 40 psi. At all aerosolization rates (AR) between 0.5 and 3 ml/min, the MMAD of the aerosols generated by and processed with heliox is below 3 μm for both the PVP solutions and surfactant suspensions (FIG. 10). When surfactant is aerosolized, the particle size appears almost independent of flow rate in the range of 1 to 3 ml/min. The geometric standard deviation, σg, was in the range of 1.7-2.2 in the case of air, while it was in the range of 1.9-2.7 in the case of heliox.

Figure 11:
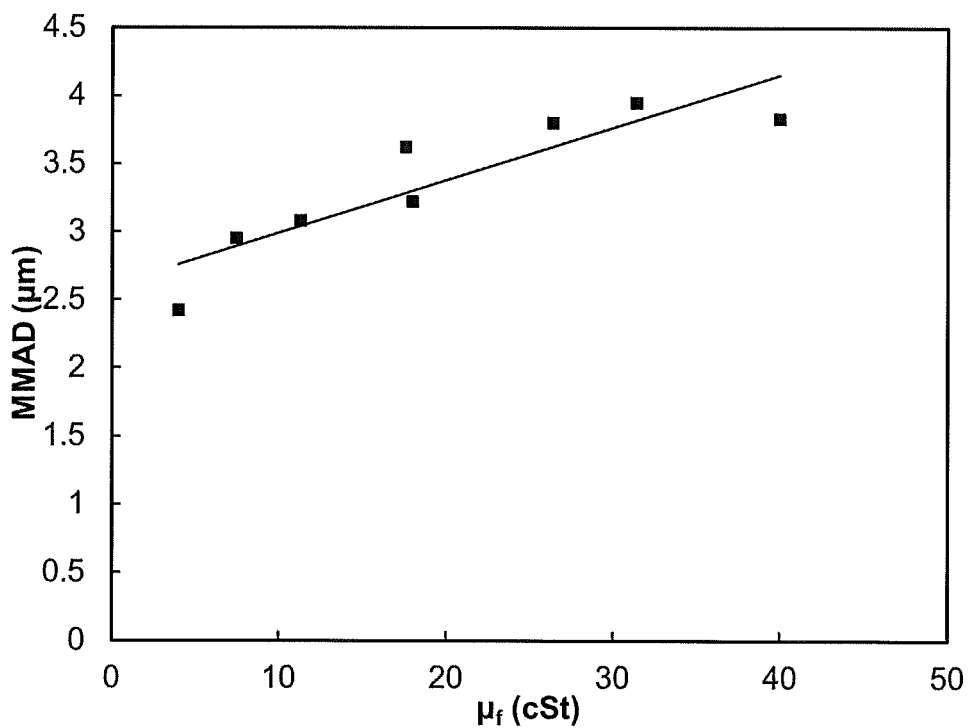
FIG. 11 shows a diagram demonstrating the influence of the viscosity ($\mu_f$) of the fluid to be aerosolized in cSt on the mass median aerodynamic diameter (MMAD) of the aerosol particles in μm.

As the viscosity of surfactant suspensions increases rapidly with increasing surfactant concentration was evaluated the effect of fluid viscosity on particles size using heliox as the aerosol generation and processing gas. The viscosities of 10% and 20% solutions of PVP of nominal molecular weights of 8, 29, 40 and 58 kDa were measured with a capillary rheometer and expressed in cSt. The Ohnesorge number, Oh, is proportional to the liquid dynamic viscosity. At large Oh (Oh>0.01), the liquid deformation and breakup are inhibited due to increased damping by liquid viscous forces. Using nozzle KB-N-700 at compressed heliox pressure of 40 psi to aerosolize PVP solutions at 1 ml/min the MMAD there was a modest increase in particle size with increasing viscosity ($\mu_f$) between 4 and 39 cSt (FIG. 11). Albeit, not included in FIG. 11, the viscosity is not limited to fluids under 39 cSt and may extend up to 100 cSt. It is notable that the highest viscosity of solutions aerosolized by some mesh-type nebulizers is <4 cSt. Thus, the incident invention markedly extends the range of large molecule and viscous solutions from which fine particle aerosols can be readily generated and delivered.

To examine the aerosol particles output efficiency by air and heliox using the cylindrical radial multi-slit aerosol concentrator, 10% PVP solution and 9.33% surfactant suspension were aerosolized with the KB-N-500 nozzle at 40 psi and collected with a respirable dry powder aerosol volume flow of 44 l/min. It can be seen in Table 1 that the output of 10% PVP increases to 192 mg/min at 3 ml/min. The output was marginally increased to 198 mg/min with heliox despite the predictable decrease in particle size. When heliox is used as the aerosolizing gas, the output efficiencies for surfactant and PVP were essentially identical.

TABLE 1

The PVP and surfactant mass output rate and efficiency for PVP and surfactant aerosols by air and heliox.

| | Aerosolization rate ml/min | Dose rate/efficiency mg/min/% | |
|---|---|---|---|
| | | Air | heliox |
| 10% 8 kDa PVP | 1 | 64/64 | 66/66 |
| | 2 | 128/64 | 132/66 |
| | 3 | 192/64 | 198/66 |
| 9.33% Surfactant | 1 | 59/63 | 62/66 |
| | 2 | 118/63 | 123/66 |
| | 3 | 165/59 | 182/65 |

To demonstrate that large masses of particles could be processed using the cylindrical radial multi-slit aerosol concentrator 10 ml and 20 ml 10% 8 kDa PVP solution at an aerosolization rate of 3 ml/min with nozzle KB-N-500 at compressed air pressure of 40 psi. Output masses of, 07 and 1.2 g were collected in 3.3 and 6.7 min, respectively. These data demonstrate that potentially clinically relevant doses of surfactant and other molecules can be delivered with the incident invention.

In the second configuration of the incident invention, the single slit aerosol concentrator replaced the cylindrical radial multi-slit aerosol concentrator to evaluate the effect of CGP on MMAD, the effect of increasing aerosolization rates on the dose rate (DR), as well as to evaluate the effects of respirable dry powder aerosol volume flow (RAVF) on the output mass concentration (MC) and the output efficiency (OE) of the aerosol processing system. The first intermediate dry powder aerosol volume flow in these experiments were 160-200 l/min and respirable dry powder aerosol volume flow was 12-44 l/min.

Figure 12:
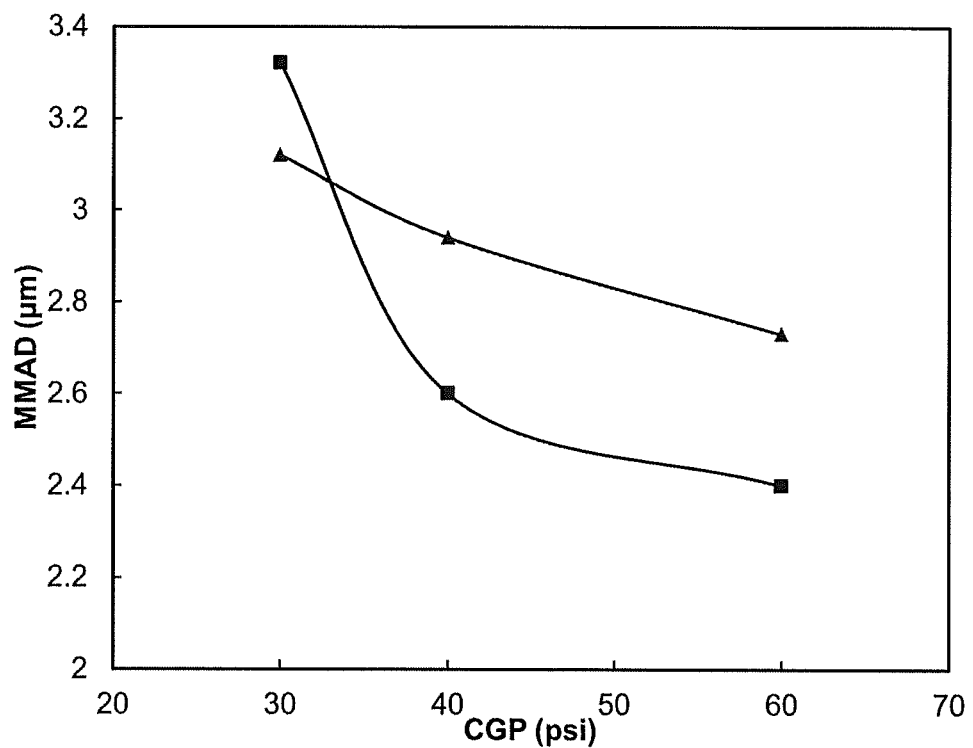
FIG. 12 shows a diagram demonstrating the influence of the compressed gas pressure (CGP) on the mass median aerodynamic diameter (MMAD) of the aerosol particles in μm for both 10% 8 kDa PVP solutions and 8.85% surfactant suspensions at an aerosolization rate (AR) 3 ml/min by using a cylindrical single linear slit aerosol concentrator. The triangular and square dots denote the aerosols generated from 10% 8 kDa PVP (heliox), 8.85% surfactant (heliox), respectively.

Aerosols were generated with heliox with nozzle KB-N-500 at an aerosolization rate 3 ml/min to aerosolize 10% 8 kDa PVP solutions and 8.85% surfactant suspensions. In both cases, the MMAD decreased with increasing CGP (FIG. 12). For comparison, the aerosol particle size, generated with air at 40 psi with the same nozzle and the same aerosolization rate from 10% 8 kDa PVP solution, was 4.1 μm.

Figure 13:
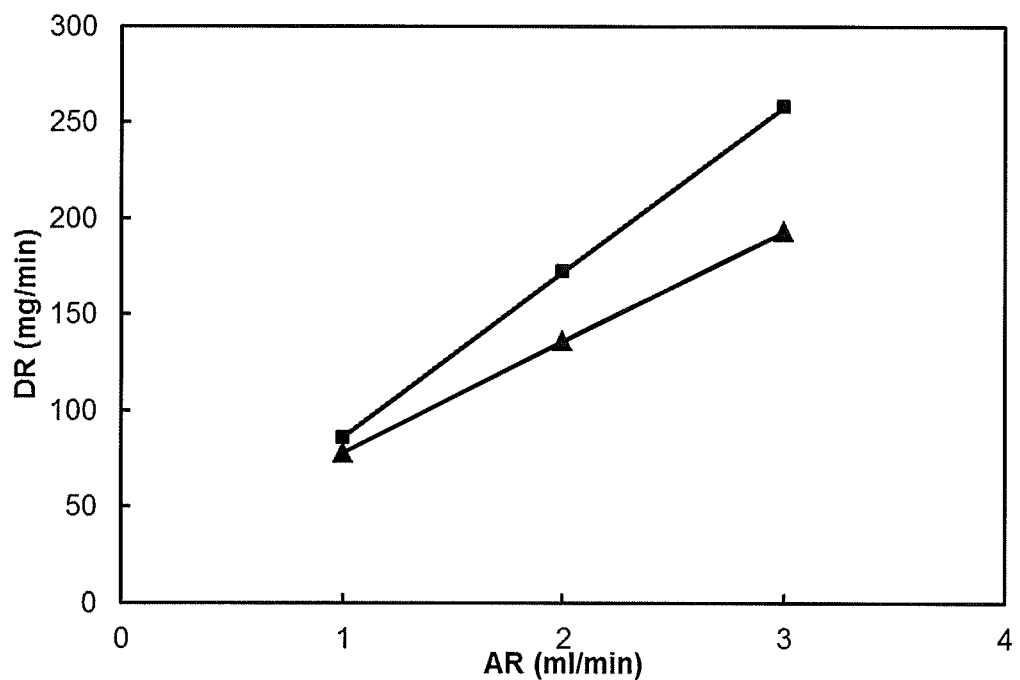
FIG. 13 shows a diagram demonstrating the influence of the aerosolization rate (AR) on the dose rate (DR) in mg/min for both 10% 8 kDa PVP solutions and 9.33% surfactant suspensions by using cylindrical single linear slit aerosol concentrator. The square and triangular dots denote the aerosols generated from 10% 8 kDa PVP (heliox), 9.33% surfactant (heliox), respectively.

The single slit aerosol concentrator used with heliox with the respirable dry powder aerosol volume flow of 44 l/min delivered particles of PVP up to 258 mg/min with the efficiency up to 86% (FIG. 13). At an aerosolization rate of 1 ml/min, the output mass concentration of surfactant was 78 mg/min (84% efficiency) and at 3 ml/min the output mass concentration 207 mg/min. Thus, there was a marked improvement in the concentration of aerosols with the use of heliox together with the cylindrical linear single slit aerosol concentrator compared to that obtained with the cylindrical radial multi-slit aerosol concentrator (Table 1).

To demonstrate that large masses of particles could be processed using the single slit aerosol concentrator 10 ml and 30 ml of 10% 8 kDa PVP were aerosolized at 3 ml/min using nozzle KB-N-500 at compressed heliox pressure of 40 psi. Output masses of 0.86 g and 2.2 g were collected at output in 3.3 min and 10 min, respectively.

These data demonstrate that the incident invention has the potential to provide 3 mg/s of particles less than 3 μm MMAD throughout each and every breath with total output doses of ~2 g of surfactant in ~10 minutes. Using the cylindrical linear single slit aerosol concentrator, the aerosol deposition on the orifices was minimal. Aerosol losses to the walls of the cylindrical linear single slit aerosol concentrator were minimal with the diverging output channel having the highest wall deposition. This particle-wall interaction on the diverging output channel at these very high particle concentrations did not appear to effect the performance of the concentrator over the ranges of particles sizes, concentrations and total masses processed reported herein. Thus, using the cylindrical linear single slit aerosol concentrator with heliox enabled higher total particle masses to be concentrated than with the cylindrical radial multi-slit concentrator.

To attain high particle concentrations, the relative utilities of the third configuration using cylindrical radial multi-slit aerosol concentrator and the fourth configuration comprising a series combination of the cylindrical radial multi-slit aerosol concentrator and the cylindrical linear single slit aerosol concentrator to form a two-stage concentrator were evaluated at a high ratio of first intermediate dry powder aerosol volume flow to respirable dry powder aerosol volume flow. The respirable dry powder aerosol volume flow of 12 l/min was chosen.

The third configuration using cylindrical radial multi-slit aerosol concentrator was evaluated using air as the aerosol generating and dilution gas. Using nozzle KB-N-400 and a fluid flow of 1 ml/min of 10% 8 kDa PVP together with a first intermediate dry powder aerosol volume flow of 80 l/min the output mass concentration was 2.2 mg/l with an output efficiency of 26% with an estimated MMAD of 3.3 μm. The output pressure was 0.4 cm of water. When the total first intermediate dry powder aerosol volume flow was increased to 160 l/min, the mass concentration was 1.5 mg/l with an output efficiency of <20%. It is notable that when an aerosol was generated from 5% 8 kDa PVP using the KB-N-400 nozzle together with the cylindrical linear single slit aerosol concentrator and a total airflow of 60 l/min and an aerosolization rate of 0.5 ml/min a mass concentration of 0.9 mg/l was attained. The pressure at the output was 6 cm of water. The MMAD was estimated at about 2.9 μm.

The fourth configuration comprising the two-stage concentrator was evaluated using air. The first intermediate dry powder aerosol volume flow of 160 l/min of air and a respirable dry powder aerosol volume flow limited to 12 l/min was evaluated. In this case, when using nozzle KB-N-500 and an aerosolization rate of 3 ml/min of 10% 8 kDa PVP, the mass concentration was 9.3 mg/l with the over al two stage concentrator output efficiency of 37%. The output pressure was 1.5 cm of water. The MMAD was about 3.2 μm.

Figure 14:
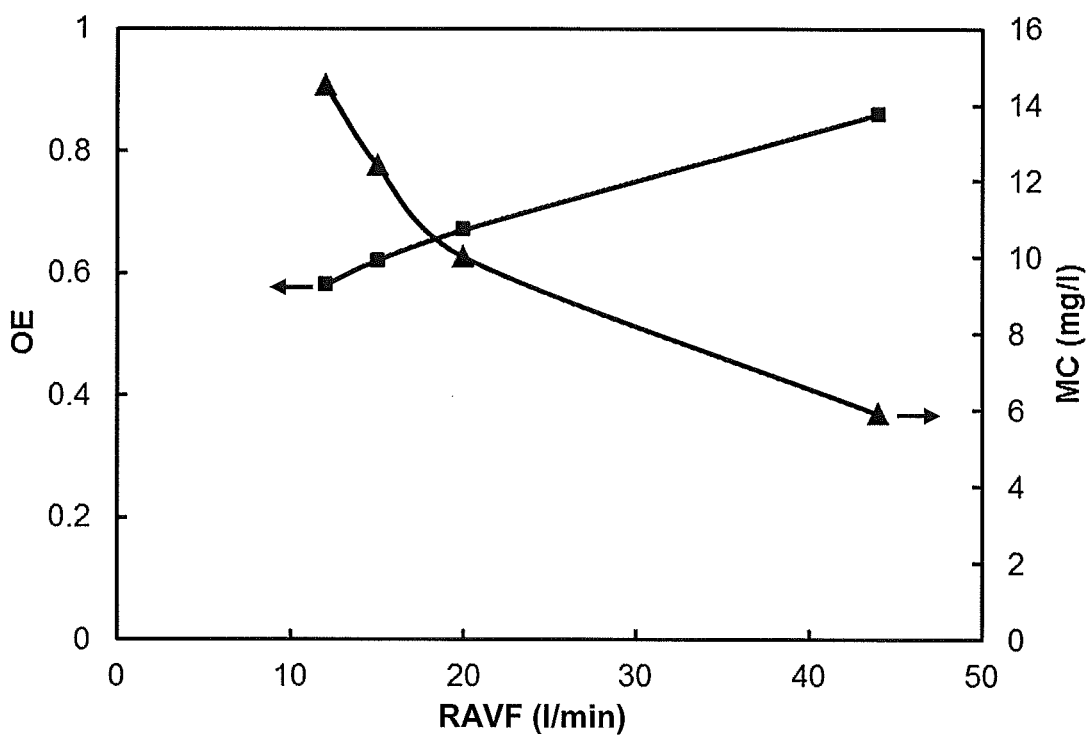
FIG. 14 shows a diagram demonstrating the influence of the respirable dry powder aerosol volume flow (RAVF) on the output efficiency (OE) and mass concentration (MC) by using cylindrical single linear slit aerosol concentrator.

Additionally, using the second configuration with heliox as the processing gas together with nozzle KB-N-500 and with cylindrical linear single slit aerosol concentrator, the first intermediate dry powder aerosol volume flow of 160-200 l/min and the respirable dry powder aerosol volume flow limited to 12 l/min and an aerosolization rate of 3 ml/min the output mass concentration was 14.5 mg/l with an output efficiency of 58% (FIG. 14). The output pressure was just 15 cm of water. The MMAD was approximately 2.9 μm.

Together, these data demonstrate that it is advantageous to use the two-stage concentrator when generating high concentrations of aerosol with air. It is notable that when heliox is available, the efficiency and output of the single stage cylindrical linear single slit aerosol concentrator is far superior, especially when aerosols of 2-3 μm MMAD are being generated.

The partioning gas flows within the fourth configuration comprising the two-stage concentrator was evaluated using either air or heliox in the absence of aerosolization. When operating in this mode with air with a first intermediate dry powder volume flow of 160 l/min, the ratio of the first intermediate aerosol dry powder aerosol volume flow to second intermediate dry powder volume flow was estimated as 2.7 for the cylindrical radial multi-slit aerosol concentrator. The ratio of the second intermediate dry powder volume flow to respirable dry powder volume flow was estimated to be 4.9 for the cylindrical linear single slit aerosol concentrator. When using this two-stage configuration was operated with heliox using the first intermediate dry powder aerosol volume flow of 210 l/min and respirable dry powder aerosol volume flow limited to 12 l/min, the input flow/output gas flows were 4.9 for the cylindrical radial multi-slit aerosol concentrator first stage and 3.6 for the cylindrical linear single slit aerosol concentrator with an overall two-stage concentrator efficiency of 41%. The output pressure was 0.6 cm. This demonstrates the versatility and practical utility of this two-stage concentrator.

Assuming that spherical particles with an ideal lognormal distribution were generated, the number of PVP/surfactant particles per liter of heliox for an aerosol of 2.6 μm ($\sigma_g$=1.9) in diameter was calculated to be $9.8 \times 10^9$, at 14.5 mg/l on the basis of the theory developed by Hatch and Choate. Subsequently, based on the Smoluchowski's approach, the number of particles would decrease due to coagulation by 0.06% after 0.2 sec. Thus, at these concentrations, the effect of coagulation can be neglected in the incident invention.

The surface tensions of the surfactant prior to and following aerosolization by SUPRAER were measured with Contact Angle Analyzer (FTA-200) using the pendant drop shape method. The static surface tensions of 4 mg/ml surfactant prior to and following aerosolization by the incident invention were 22.2 and 22.6 mN/m, respectively. The aerosolization and resuspension processes did not degrade the surface tension of the surfactant.

Use and Application of the Embodiments of the Invention

These data demonstrate the remarkable efficiency of this configuration of the incident invention to deliver high doses of fine particle aerosols 1.5 μm to 4 μm MMAD with 1.6-2.7 geometric standard deviations. The incident invention is able to meet the aerosol delivery needs of adults, children and infants. It also lends itself to the extremely rapid emergency delivery of therapeutic aerosols in other life threatening conditions.

Through the use of the cylindrical linear single slit aerosol concentrator, in conjunction with the use of heliox ability to generate aerosols <3 μm mass median aerodynamic diameter, MMAD, from a 9.33% surfactant suspension (viscosity 34 cP) was accomplished and deliver high payloads of dry powder aerosols containing up to 3 mg/s of pure phospholipids with efficiencies between 69% and 84%. The low surface tension properties of the surfactant are retained following aerosolization and resuspension. The incident invention has the potential to deliver a constant 3 mg/s throughout each and every inspiration over the entire treatment time without interruption. The surfactant dose rate and total dose are 10 to 20 times higher than that attainable by competitive devices. For the first time, a clinically relevant dose of aerosolized surfactant will be attainable for multiple treatments in adults with impaired lung function. Thus this incident invention, together with a surfactant that contains the SPB protein (or mimetic), has the potential to provide life-saving physiological benefits to enable the resolution of the pulmonary inflammatory processes.

According to the invention, heliox more efficiently generates and delivers surfactant aerosols than air. In addition, heliox facilitates deeper penetration of aerosols into the lungs and improves gas exchange, especially in patients with compromised lung function. The physical properties of heliox have enabled us to deliver <3 μm MMAD aerosols at efficiencies up to 86% using cylindrical linear single slit aerosol concentrator, while the efficiency was 69% in the case of air. The lower losses enable us to realize higher total delivered doses of surfactant. Moreover, the process of evaporating water from the aerosols was enhanced due to the fact that heliox has a higher thermal conductivity and specific heat than air. This has enables surfactant to be delivered with high efficiencies even at high delivered doses. When the cylindrical linear single slit aerosol concentrator is used with air rather than heliox at these flow rates (First intermediate dry powder aerosol volume flow: 160-200 l/min; respirable dry powder aerosol volume flow: 44 l/min), the delivered pressure to the patients would be higher than 38 cm $H_2O$, while this pressure is only 13 cm $H_2O$ when heliox is used. The high aerosol delivery pressure when air is used with the cylindrical linear single slit aerosol concentrator is both undesirable for patients breathing spontaneously and sets a too high lower limit on ventilation with continuous positive airway pressure, CPAP, or positive end expiratory pressure, PEEP, when using in the intensive care unit setting. The cylindrical radial multi-slit aerosol concentrator, when used with air, has an aerosol delivery pressure as low as 3 cm $H_2O$ and has efficiencies between 59 and 64%. To provide a unit to address the needs of clinical facilities that do not have heliox, or choose not to use it, according to the invention as described above it was possible to use in connection with the some of the described embodiments either air or heliox as the aerosol generating and processing gas.

Further embodiments 1-141 of the invention are described in the following:

1. An aerosol generating system for generating a respirable dry powder aerosol 15 from a liquid solution or liquid suspension at a respirable dry powder aerosol volume flow 91, comprising:
    a liquid aerosol generating nozzle 3 having a nozzle input end 11 designed to receive the liquid solution or liquid suspension, and having a nozzle gas supply 55 designed to receive nozzle gas 2, the liquid aerosol generating nozzle 3 further having a nozzle output end 36 for outputting a liquid aerosol 13 suspended in the nozzle gas 2;
    a cylindrical evaporation chamber 6 having a cylindrical evaporation chamber input end 7 that is connected to the nozzle output end 36 and connected to a dilution gas supply 60 for receiving both the liquid aerosol 13 suspended in the nozzle gas 2 and for receiving the dilution gas 4, and the cylindrical evaporation chamber 6 having a cylindrical evaporation chamber output end 8 outputting a first intermediate dry powder aerosol 14 at a first intermediate dry powder aerosol volume flow 89 and a first intermediate dry powder aerosol particle concentration 90; and a cylindrical single linear slit aerosol concentrator 9 having a cylindrical single linear slit aerosol concentrator input end 10 that is connected to the cylindrical evaporation chamber output end 8, the cylindrical single linear slit aerosol concentrator 9 comprising a converging cylindrical single linear slit aerosol concentrator input channel 19 converging from the cylindrical single linear slit aerosol concentrator input end 10 to a cylindrical single linear slit aerosol concentrator input orifice 20 that is connected to a cylindrical single linear slit aerosol concentrator aerosol separation space 40, the cylindrical single linear slit aerosol concentrator aerosol separation space 40 connecting both to a cylindrical single linear slit aerosol concentrator exhaust port 44 and to a cylindrical single linear slit aerosol concentrator output orifice 21, the cylindrical single linear slit aerosol concentrator output orifice 21 being connected to a diverging cylindrical single linear slit aerosol concentrator output channel 22 outputting the respirable dry powder aerosol 15 at the respirable dry powder aerosol volume flow 91 that is lower than the first intermediate dry powder aerosol volume flow 89 and at a respirable dry powder aerosol particle concentration 92 that is higher than the first intermediate dry powder aerosol particle concentration 90.

2. The system according to embodiment claim 1 wherein at least one of the nozzle gas 2 and the dilution gas 4 is heliox.

3. The system according to embodiment 1 wherein at least one of the nozzle gas 2 and the dilution gas 4 is air.

4. The system according to one of the preceding embodiments 1-3 wherein the first intermediate dry powder aerosol volume flow 89 is between 80 and 200 l/min.

5. The system according to one of the preceding embodiments 1-4 wherein the cylindrical single linear slit aerosol concentrator output orifice 21 is between 1 and 5 cm long and between 1 and 2 mm wide.

6. The system according to one of the preceding embodiments 1-5 wherein the liquid solution or liquid suspension contains a surfactant.

7. The system according to one of the preceding embodiments 1-6 wherein the cylindrical single linear slit aerosol concentrator 9 has a cylindrical single linear slit aerosol concentrator aerosol separation space 40 that is less than 2 mm wide and extends between a cylindrical single linear slit aerosol concentrator input orifice 20 and the cylindrical single linear slit aerosol concentrator output orifice 21.

8. The system according to one of the preceding embodiments 1-7 wherein the converging cylindrical single linear slit aerosol concentrator input channel 19 converges from the cylindrical single linear slit aerosol concentrator input end 10 to a center of the cylindrical single linear slit aerosol concentrator input orifice 20 at a converging cylindrical single linear slit aerosol concentrator input channel angle 52 between 10 and 60 degrees.

9. The system according to one of the preceding embodiments 1-8 wherein the diverging cylindrical single linear slit aerosol concentrator output channel 22 diverges from the cylindrical single linear slit aerosol concentrator output orifice 21 at a diverging cylindrical single linear slit aerosol concentrator output channel angle 53 between 10 and 60 degrees.

10. The system according to one of the preceding embodiments 1-9 further comprising a sculptured plenum 43 that connects the cylindrical single linear slit aerosol concentrator aerosol separation space 40 and the cylindrical single linear slit aerosol concentrator exhaust port 44 and has a sculptured plenum volume between 30 and 300 ml.

11. The system according to one of the preceding embodiments 1-10 wherein the cylindrical single linear slit aerosol concentrator exhaust port 44 with a diameter of 10-20 mm.

12. The system according to one of the preceding embodiments 1-11 wherein in use the cylindrical single linear slit aerosol concentrator input orifice 20 and the cylindrical single linear slit aerosol concentrator output orifice 21 extend substantially vertically.

13. The system according to one of the preceding embodiments 1-12 wherein the system is designed to output from the cylindrical evaporation chamber 6 the first intermediate dry powder aerosol 14 having fine particles of a size of 1.5-4 µm MMAD suspended in gas.

14. The system according to one of the preceding embodiments 1-13 wherein the system is designed to aerosolize the liquid solution or liquid suspension having a liquid solution or liquid suspension viscosity of 4 to 39 cSt.

15. The system according to one of the preceding embodiments 1-14 wherein the nozzle gas 2 has a nozzle gas pressure between 207 and 414 kPa.

16. The system according to embodiment 2 wherein the respirable dry powder aerosol 15 has a respirable dry powder aerosol pressure of less than 1 cm of water.

17. The system according to embodiment 3 wherein the respirable dry powder aerosol 15 has a respirable dry powder aerosol pressure of less than 2 cm of water.

18. The system according to one of the preceding embodiments 1-17 wherein the respirable dry powder aerosol volume flow 91 is 10-15 l/min while concentration efficiency is greater than 30%.

19. The system according to one of the preceding embodiments 1-18 wherein the system is free of flow controls at the cylindrical single linear slit aerosol concentrator exhaust port 44 of the cylindrical single linear slit aerosol concentrator 9.

20. The system according to one of the preceding embodiments 1-19 further comprising a counter flow tube 54, an infrared radiation source 39, a reflector 72, and an aerosol collection cone 95.

21. The system according to one of the preceding embodiments 1-20 wherein the system is designed to receive the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 µm or less.

22. The system according to embodiment 21 wherein the system is designed to receive the liquid solution or liquid suspension at a liquid solution or suspension viscosity exceeding 4 cSt.

23. The system according to embodiment 22 wherein the system is designed to output the respirable dry powder aerosol volume flow 91 between 12 l/min and 44 l/min, thereby delivering a medication at a medication mass concentration of at least 5 mg/l and up to 14.5 mg/l.

24. A method for generating a respirable dry powder aerosol 15 from a liquid solution or liquid suspension at a respirable dry powder aerosol volume flow 91, comprising:
  feeding liquid solution or liquid suspension and nozzle gas 2 into a liquid aerosol generating nozzle 3;
  outputting from the liquid aerosol generating nozzle 3 a liquid aerosol 13 suspended in the nozzle gas 2 into a cylindrical evaporation chamber 6;
  feeding dilution gas 4 into the cylindrical evaporation chamber 6;
  outputting from the cylindrical evaporation chamber 6 a first intermediate dry powder aerosol 14 having fine dry powder particles that allow respirable particles containing a medically active agent and are suspended in gas at a first intermediate dry powder aerosol volume flow 89 and a first intermediate dry powder aerosol particle concentration 90;
  feeding the first intermediate dry powder aerosol 14 into a cylindrical single linear slit aerosol concentrator 9, the cylindrical single linear slit aerosol concentrator 9 comprising a converging cylindrical single linear slit aerosol concentrator input channel 19 converging to a cylindrical single linear slit aerosol concentrator input orifice 20 and a diverging cylindrical single linear slit aerosol concentrator output channel 22 diverging from a cylindrical single linear slit aerosol concentrator output orifice 21; and
  outputting the respirable dry powder aerosol 15 at the respirable dry powder aerosol volume flow 91 that is lower than the first intermediate dry powder aerosol volume flow 89 and a respirable dry powder aerosol particle concentration 92 that is higher than the first intermediate dry powder aerosol particle concentration 90.

25. The method according to embodiment 24 further comprising supplying heliox as at least one of the nozzle gas 2 and the dilution gas 4.

26. The method according to embodiment 24 further comprising supplying air as at least one of the nozzle gas 2 and the dilution gas 4.

27. The method according to one of the preceding embodiments 24-26 further comprising generating the first intermediate dry powder aerosol volume flow 89 at between 80 and 200 l/min.

28. The method according to one of the preceding embodiments 24-27 further comprising providing the cylindrical single linear slit aerosol concentrator output orifice 21 with a length between 1 and 5 cm and a width between 1 and 2 mm.

29. The method according to one of the preceding embodiments 24-28 further comprising providing a surfactant as a constituent of the liquid solution or liquid suspension.

30. The method according to one of the preceding embodiments 24-29 further comprising providing the cylindrical single linear slit aerosol concentrator 9 with a cylindrical single linear slit aerosol concentrator aerosol separation space 40 that is less than 2 mm wide and extends between the cylindrical single linear slit aerosol concentrator input orifice 20 and the cylindrical single linear slit aerosol concentrator output orifice 21.

31. The method according to one of the preceding embodiments 24-30 further comprising providing the converging cylindrical single linear slit aerosol concentrator input channel 19 so that it converges from the cylindrical single linear slit aerosol concentrator input end 10 to a center of the cylindrical single linear slit aerosol concentrator input orifice 20 at a converging cylindrical single linear slit aerosol concentrator input channel angle 52 between 10 and 60 degrees.

32. The method according to one of the preceding embodiments 24-31 further comprising providing the diverging cylindrical single linear slit aerosol concentrator output channel 22 so that it diverges from the cylindrical single linear slit aerosol concentrator output orifice 21 at a diverging cylindrical single linear slit aerosol concentrator output channel angle 53 between 10 and 60 degrees.

33. The method according to one of the preceding embodiments 24-32 further comprising providing a sculptured plenum 43 that connects the cylindrical single linear slit aerosol concentrator aerosol separation space 40 and the cylindrical single linear slit aerosol concentrator exhaust port 44 and has a sculptured plenum volume between 30 and 300 ml.

34. The method according to one of the preceding embodiments 24-33 further comprising providing the cylindrical single linear slit aerosol concentrator exhaust port 44 with a diameter of 10-20 mm.

35. The method according to one of the preceding embodiments 24-34 further comprising positioning the cylindrical single linear slit aerosol concentrator input orifice 20 and the cylindrical single linear slit aerosol concentrator output orifice 21 such that these extend substantially vertically.

36. The method according to one of the preceding embodiments 24-35 further comprising outputting from the cylindrical evaporation chamber 6 the first intermediate dry powder aerosol 14 at a fine particles of a size of 1.5-4 μm MMAD suspended in gas.

37. The method according to one of the preceding embodiments 24-36 further comprising aerosolizing the liquid solution or liquid suspension having a liquid solution or liquid suspension viscosity of 4 to 39 cSt.

38. The method according to one of the preceding embodiments 24-37 further comprising supplying the nozzle gas 2 at a nozzle gas 2 pressure between 207 and 414 kPa.

39. The method according to embodiment 25 further comprising generating the respirable dry powder aerosol 15 at a respirable dry powder aerosol pressure of less than 1 cm of water.

40. The method according to embodiment 26 further comprising generating the respirable dry powder aerosol 1 at a respirable dry powder aerosol pressure of less than 2 cm of water.

41. The method according to one of the preceding embodiments 24-40 further comprising generating the respirable dry powder aerosol volume flow 91 at 10-15 l/min while concentration efficiency is greater than 30%.

42. The method according to one of the preceding embodiments 24-41 further comprising omitting any flow controls at the single linear slit aerosol concentrator exhaust port 44 of the cylindrical single linear slit aerosol concentrator 9.

43. The method according to one of the preceding embodiments 24-42 further comprising providing a counter flow tube 54, an infrared radiation source 39, a reflector 72, and an aerosol collection cone 79.

44. The method according to one of the preceding embodiments 24-43 further comprising supplying the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 μm or less.

45. The method according to embodiment 44 further comprising supplying the liquid solution or liquid suspension at a liquid solution or suspension viscosity exceeding 4 cSt.

46. The method according to embodiment 45 wherein the method is designed to output the respirable dry powder aerosol volume flow 91 between 12 l/min and 44 l/min, thereby delivering a medication at a medication mass concentration of at least 5 mg/l and up to 14.5 mg/l.

47. The method according to one of the preceding embodiments 24-46 further comprising controlling the volume flow ratios such that the ratio of the first intermediate dry powder aerosol volume flow 89 to the respirable dry powder volume flow 91 is less than 5.

48. An aerosol generating system for generating a respirable dry powder aerosol 15 from a liquid solution or liquid suspension at a respirable dry powder aerosol volume flow 91, comprising:

a liquid aerosol generating nozzle 3 having a nozzle input end 11 designed to receive the liquid solution or liquid suspension, and having a nozzle gas supply 55 designed to receive nozzle gas 2, the liquid aerosol generating nozzle 3 further having a nozzle output end 36 for outputting a liquid aerosol 13 suspended in the nozzle gas 2;

a cylindrical evaporation chamber 6 having a cylindrical evaporation chamber input end 7 that is connected to the nozzle output end 36 and connected to a dilution gas supply 60 for receiving both the liquid aerosol 13 suspended in the nozzle gas 2 and for receiving the dilution gas 4, and the cylindrical evaporation chamber 6 having a cylindrical evaporation chamber output end 8 outputting a first intermediate dry powder aerosol 14 at a first intermediate dry powder aerosol volume flow 89 and a first intermediate dry powder aerosol particle concentration 90;

a cylindrical radial multi-slit aerosol concentrator 24 comprising at least 3 slits extending from a position at or close to a center of the cylindrical radial multi-slit aerosol concentrator 24 to a position more remote from the center of the cylindrical radial multi-slit aerosol concentrator 24, the cylindrical radial multi-slit aerosol concentrator 24 having a cylindrical radial multi-slit aerosol concentrator input end 25 that is connected to the cylindrical evaporation chamber output end 8, and a cylindrical radial multi-slit aerosol concentrator output end 26 outputting a second intermediate dry powder aerosol 17 at a second intermediate dry powder aerosol volume flow 93 and a second intermediate dry powder aerosol particle concentration 94, the second intermediate dry powder aerosol volume flow 93 being lower than the first intermediate dry powder aerosol volume flow 89 and the second intermediate dry powder aerosol particle concentration 94 being higher than the first intermediate dry powder aerosol particle concentration 90; and a cylindrical single linear slit aerosol concentrator 9 having a cylindrical single linear slit aerosol concentrator input end 10 that is connected to the cylindrical radial multi-slit aerosol concentrator output end 26, the cylindrical single linear slit aerosol concentrator 9 comprising a converging cylindrical single linear slit aerosol concentrator input channel 19 converging from the cylindrical single linear slit aerosol concentrator input end 10 to a cylindrical single linear slit aerosol concentrator input orifice 20 that is connected to a cylindrical single linear slit aerosol concentrator aerosol separation space 40, the cylindrical single linear slit aerosol concentrator aerosol separation space 40 connecting both to a cylindrical single linear slit aerosol concentrator exhaust port 44 and to a cylindrical single linear slit aerosol concentrator output orifice 21, the cylindrical single linear slit aerosol concentrator output orifice 21 being connected to a diverging cylindrical single linear slit aerosol concentrator output channel 22 outputting the respirable dry powder aerosol 15 at the respirable dry powder aerosol volume flow 91 that is lower than the second intermediate dry powder aerosol volume flow 93 and a respirable dry powder aerosol particle concentration 92 that is higher than the second intermediate dry powder aerosol particle concentration 94.

49. The system according to embodiment 48 wherein at least one of the nozzle gas 2 and the dilution gas 4 is heliox.

50. The system according to embodiment 48 wherein at least one of the nozzle gas 2 and the dilution gas 4 is air.

51. The system according to one of the preceding embodiments 48-50 wherein the first intermediate dry powder aerosol volume flow 89 is between 80 and 200 l/min.

52. The system according to one of the preceding embodiments 48-51 wherein the cylindrical single linear slit aerosol concentrator output orifice 21 is between 1 and 5 cm long and between 1 and 2 mm wide.

53. The system according to one of the preceding embodiments 48-52 wherein the liquid solution or liquid suspension contains a surfactant.

54. The system according to one of the preceding embodiments 48-53 wherein the cylindrical single linear slit aerosol concentrator 9 has a cylindrical single linear slit aerosol concentrator aerosol separation space 40 that is less than 2 mm wide and extends between a cylindrical single linear slit aerosol concentrator input orifice 20 and the cylindrical single linear slit aerosol concentrator output orifice 21.

55. The system according to one of the preceding embodiments 48-54 wherein the converging cylindrical single linear slit aerosol concentrator input channel 19 converges from the cylindrical single linear slit aerosol concentrator input end 10 to a center of the cylindrical single linear slit aerosol concentrator input orifice 20 at a converging cylindrical single linear slit aerosol concentrator input channel angle 52 between 10 and 60 degrees.

56. The system according to one of the preceding embodiments 48-55 wherein the diverging cylindrical single linear slit aerosol concentrator output channel 22 diverges from the cylindrical single linear slit aerosol concentrator output orifice 21 at a diverging cylindrical single linear slit aerosol concentrator output channel angle 53 between 10 and 60 degrees.

57. The system according to one of the preceding embodiments 48-56 further comprising a sculptured plenum 43 that connects the cylindrical single linear slit aerosol concentrator aerosol separation space 40 and the cylindrical single linear slit aerosol concentrator exhaust port 44 and has a sculptured plenum volume between 30 and 300 ml.

58. The system according to one of the preceding embodiments 48-57 wherein the cylindrical single linear slit aerosol concentrator exhaust port 44 with a diameter of 10-20 mm.

59. The system according to one of the preceding embodiments 48-58 wherein in use the cylindrical single linear slit aerosol concentrator input orifice 20 and the cylindrical single linear slit aerosol concentrator output orifice 21 extend substantially vertically.

60. The system according to one of the preceding embodiments 48-59 wherein the system is designed to output from the cylindrical evaporation chamber 6 the first intermediate dry powder aerosol 14 having fine particles of a size of 1.5-4 μm MMAD suspended in gas.

61. The system according to one of the preceding embodiments 48-60 wherein the system is designed to aerosolize the liquid solution or liquid suspension having a liquid solution or liquid suspension viscosity of 4 to 39 cSt.

62. The system according to one of the preceding embodiments 48-61 wherein the nozzle gas 2 has a nozzle gas pressure between 207 and 414 kPa.

63. The system according to embodiment 49 wherein the respirable dry powder aerosol 15 has a respirable dry powder aerosol pressure of less than 1 cm of water.

64. The system according to embodiment 50 wherein the respirable dry powder aerosol 15 has a respirable dry powder aerosol pressure of less than 2 cm of water.

65. The system according to one of the preceding embodiments 48-64 wherein a total cylindrical radial multi-slit aerosol concentrator slit length of the cylindrical radial multi-slit aerosol concentrator 24 is at least 4 times longer than a cylindrical single linear slit aerosol concentrator slit length of the cylindrical single linear slit aerosol concentrator 9.

66. The system according to one of the preceding embodiments 48-65 wherein the respirable dry powder aerosol volume flow 91 is 10-15 l/min while concentration efficiency is greater than 30%.

67. The system according to one of the preceding embodiments 48-66 wherein the system is free of flow controls at a cylindrical radial multi-slit aerosol concentrator exhaust port 51 of the cylindrical radial multi-slit aerosol concentrator 24 and the cylindrical single linear slit aerosol concentrator exhaust port 44 of the cylindrical single linear slit aerosol concentrator 9.

68. The system according to one of the preceding embodiments 48-67 further comprising a counter flow tube 54, an infrared radiation source 39, a reflector 72, and an aerosol collection cone 95.

69. The system according to one of the preceding embodiments 48-68 wherein the system is designed to receive the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 μm or less.

70. The system according to embodiment 69 wherein the system is designed to receive the liquid solution or liquid suspension at a liquid solution or suspension viscosity exceeding 4 cSt.

71. The system according to embodiment 70 wherein the system is designed to output the respirable dry powder aerosol volume flow 91 between 12 l/min and 44 l/min, thereby delivering a medication at a medication mass concentration of at least 5 mg/l and up to 14.5 mg/l.

72. A method for generating a respirable dry powder aerosol 15 from a liquid solution or liquid suspension at a respirable dry powder aerosol volume flow 91, comprising:
feeding liquid solution or liquid suspension and nozzle gas 2 into a liquid aerosol generating nozzle 3;
outputting from the liquid aerosol generating nozzle 3 a liquid aerosol 13 suspended in the nozzle gas 2 into a cylindrical evaporation chamber 6;
feeding dilution gas 4 into the cylindrical evaporation chamber 6;
outputting from the cylindrical evaporation chamber 6 a first intermediate dry powder aerosol 14 having fine dry powder particles that allow respirable particles containing a medically active agent and are suspended in gas at a first intermediate dry powder aerosol volume flow 89 and a first intermediate dry powder aerosol particle concentration 90;
feeding the first intermediate dry powder aerosol 14 into a cylindrical radial multi-slit aerosol concentrator 24 comprising at least 3 slits extending from a position at or close to a center of the cylindrical radial multi-slit aerosol concentrator 24 to a position more remote from the center of the cylindrical radial multi-slit aerosol concentrator 24;

outputting from the cylindrical radial multi-slit aerosol concentrator 24 a second intermediate dry powder aerosol 17 at a second intermediate dry powder aerosol volume flow 93 and a second intermediate dry powder aerosol particle concentration 94, the second intermediate dry powder aerosol volume flow 93 being lower than the first intermediate dry powder aerosol volume flow 89 and the second intermediate dry powder aerosol particle concentration 94 being higher than the first intermediate dry powder aerosol particle concentration 90;

feeding the second intermediate dry powder aerosol 17 into a cylindrical single linear slit aerosol concentrator 9, the cylindrical single linear slit aerosol concentrator 9 comprising a converging cylindrical single linear slit aerosol concentrator input channel 19 converging to a cylindrical single linear slit aerosol concentrator input orifice 20 and a diverging cylindrical single linear slit aerosol concentrator output channel 22 diverging from a cylindrical single linear slit aerosol concentrator output orifice 21; and outputting the respirable dry powder aerosol 15 at the respirable dry powder aerosol volume flow 91 that is lower than the second intermediate dry powder aerosol volume flow 93 and a respirable dry powder aerosol particle concentration 92 that is higher than the second intermediate dry powder aerosol particle concentration 94.

73. The method according to embodiment 72 further comprising supplying heliox as at least one of the nozzle gas 2 and the dilution gas 4.

74. The method according to embodiment 72 further comprising supplying air as at least one of the nozzle gas 2 and the dilution gas 4.

75. The method according to one of the preceding embodiments 72-74 further comprising generating the first intermediate dry powder aerosol volume flow 89 at between 80 and 200 l/min.

76. The method according to one of the preceding embodiments 72-75 further comprising providing the cylindrical single linear slit aerosol concentrator output orifice 21 with a length between 1 and 5 cm and a width between 1 and 2 mm.

77. The method according to one of the preceding embodiments 72-76 further comprising providing a surfactant as a constituent of the liquid solution or liquid suspension.

78. The method according to one of the preceding embodiments 72-77 further comprising providing the cylindrical single linear slit aerosol concentrator 9 with a cylindrical single linear slit aerosol concentrator aerosol separation space 40 that is less than 2 mm wide and extends between the cylindrical single linear slit aerosol concentrator input orifice 20 and the cylindrical single linear slit aerosol concentrator output orifice 21.

79. The method according to one of the preceding embodiments 72-78 further comprising providing the converging cylindrical single linear slit aerosol concentrator input channel 19 so that it converges from the cylindrical single linear slit aerosol concentrator input end 10 to a center of the cylindrical single linear slit aerosol concentrator input orifice 20 at a converging cylindrical single linear slit aerosol concentrator input channel angle 52 between 10 and 60 degrees.

80. The method according to one of the preceding embodiments 72-79 further comprising providing the diverging cylindrical single linear slit aerosol concentrator output channel 22 so that it diverges from the cylindrical single linear slit aerosol concentrator output orifice 21 at a diverging cylindrical single linear slit aerosol concentrator output channel angle 53 between 10 and 60 degrees.

81. The method according to one of the preceding embodiments 72-80 further comprising providing a sculptured plenum 43 that connects the cylindrical single linear slit aerosol concentrator aerosol separation space 40 and the cylindrical single linear slit aerosol concentrator exhaust port 44 and has a sculptured plenum volume between 30 and 300 ml.

82. The method according to one of the preceding embodiments 72-81 further comprising providing the cylindrical single linear slit aerosol concentrator exhaust port 44 with a diameter of 10-20 mm.

83. The method according to one of the preceding embodiments 72-82 further comprising positioning the cylindrical single linear slit aerosol concentrator input orifice 20 and the cylindrical single linear slit aerosol concentrator output orifice 21 such that these extend substantially vertically.

84. The method according to one of the preceding embodiments 72-83 further comprising outputting from the cylindrical evaporation chamber 6 the first intermediate dry powder aerosol 14 at a fine particles of a size of 1.5-4 µm MMAD suspended in gas.

85. The method according to one of the preceding embodiments 72-84 further comprising aerosolizing the liquid solution or liquid suspension having a liquid solution or liquid suspension viscosity of 4 to 39 cSt.

86. The method according to one of the preceding embodiments 72-85 further comprising supplying the nozzle gas 2 at a nozzle gas 2 pressure between 207 and 414 kPa.

87. The method according to embodiment 73 further comprising generating the respirable dry powder aerosol 15 at a respirable dry powder aerosol pressure of less than 1 cm of water.

88. The method according to embodiment 74 further comprising generating the respirable dry powder aerosol 15 at a respirable dry powder aerosol pressure of less than 2 cm of water.

89. The method according to one of the preceding embodiments 72-88 further comprising providing as a total cylindrical radial multi-slit aerosol concentrator slit length of the cylindrical radial multi-slit aerosol concentrator 24 a length that is at least 4 times longer than the slit length of the cylindrical single linear slit aerosol concentrator 9.

90. The method according to one of the preceding embodiments 72-89 further comprising generating the respirable dry powder aerosol volume flow 91 at 10-15 l/min while concentration efficiency is greater than 30%.

91. The method according to one of the preceding embodiments 72-90 further comprising omitting any flow controls at the cylindrical radial multi-slit aerosol concentrator exhaust port 54 of the cylindrical radial multi-slit aerosol concentrator 24 and the cylindrical single linear slit aerosol concentrator exhaust port 44 of the cylindrical single linear slit aerosol concentrator 9.

92. The method according to one of the preceding embodiments 72-91 further comprising providing a counter flow tube 54, an infrared radiation source 39, a reflector 72, and an aerosol collection cone 79.

93. The method according to one of the preceding embodiments 72-92 further comprising supplying the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 μm or less.

94. The method according to embodiment 93 further comprising supplying the liquid solution or liquid suspension at a liquid solution or suspension viscosity exceeding 4 cSt.

95. The method according to embodiment 94 wherein the method is designed to output the respirable dry powder aerosol volume flow 91 between 12 l/min and 44 l/min, thereby delivering a medication at a medication mass concentration of at least 5 mg/l and up to 14.5 mg/l.

96. The method according to one of the preceding embodiments 72-95 further comprising controlling the volume flow ratios such that the ratio of the first intermediate dry powder aerosol volume flow 89 to the second intermediate dry powder volume flow 93 and the ratio of the second intermediate dry powder volume flow 93 to the respirable dry powder volume flow 91 are both less than 5.

97. An aerosol generating system for generating a respirable dry powder aerosol 15 from a liquid solution or liquid suspension, comprising:
   a liquid aerosol generating nozzle 3 having a nozzle input end 11 designed to receive the liquid solution or liquid suspension, and having a nozzle heliox supply 55 designed to receive nozzle heliox 2, the liquid aerosol generating nozzle 3 further having a nozzle output end 36 for outputting a liquid aerosol 13 suspended in the nozzle heliox 2; and
   a cylindrical evaporation chamber 6 having a cylindrical evaporation chamber input end 7 that is connected to the nozzle output end 36 and connected to a dilution heliox supply 60 for receiving both the liquid aerosol 13 suspended in the nozzle heliox 2 and for receiving the dilution heliox 4, and the cylindrical evaporation chamber 6 having a cylindrical evaporation chamber output end 8 outputting a first intermediate dry powder aerosol 14 at a first intermediate dry powder aerosol volume flow 89 and a first intermediate dry powder aerosol particle concentration 90; and
   a cylindrical radial multi-slit aerosol concentrator 24 comprising at least 3 slits extending from a position at or close to a center of the cylindrical radial multi-slit aerosol concentrator 24 to a position more remote from the center of the cylindrical radial multi-slit aerosol concentrator 24, the cylindrical radial multi-slit aerosol concentrator 24 having a cylindrical radial multi-slit aerosol concentrator input end 25 that is connected to the cylindrical evaporation chamber output end 8, and a cylindrical radial multi-slit aerosol concentrator output end 26 outputting the respirable dry powder aerosol 15 at the respirable dry powder aerosol volume flow 91 that is lower than the first intermediate dry powder aerosol volume flow 89 and a respirable dry powder aerosol particle concentration 92 that is higher than the first intermediate dry powder aerosol particle concentration 90.

98. The system according to embodiment 97 wherein the first intermediate dry powder aerosol volume flow 89 is between 80 and 200 l/min.

99. The system according to one of the preceding embodiments 97-98 wherein the liquid solution or liquid suspension contains a surfactant.

100. The system according to one of the preceding embodiments 97-99 wherein the system is designed to output from the cylindrical evaporation chamber 6 the first intermediate dry powder aerosol 14 having fine particles of a size of 1.5-4 μm MMAD suspended in gas.

101. The system according to one of the preceding embodiments 97-100 wherein the system is designed to aerosolize the liquid solution or liquid suspension having a liquid solution or liquid suspension viscosity of 4 to 39 cSt.

102. The system according to one of the preceding embodiments 97-101 wherein the nozzle heliox 2 has a heliox pressure between 207 and 414 kPa.

103. The system according to one of the preceding embodiments 97-102 wherein the respirable dry powder aerosol 15 has a respirable dry powder aerosol pressure of less than 1 cm of water.

104. The system according to one of the preceding embodiments 97-103 wherein the respirable dry powder aerosol volume flow 91 is 10-15 l/min while concentration efficiency is greater than 30%.

105. The system according to one of the preceding embodiments 97-104 wherein the system is free of flow controls at a cylindrical radial multi-slit aerosol concentrator exhaust port 51 of the cylindrical radial multi-slit aerosol concentrator 24.

106. The system according to one of the preceding embodiments 97-105 further comprising a counter flow tube 54, an infrared radiation source 39, a reflector 72, and an aerosol collection cone 95.

107. The system according to one of the preceding embodiments 97-106 wherein the system is designed to receive the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 μm or less.

108. The system according to embodiment 107 wherein the system is designed to receive the liquid solution or liquid suspension at a liquid solution or suspension viscosity exceeding 4 cSt.

109. The system according to embodiment 108 wherein the system is designed to output the respirable dry powder aerosol volume flow 91 between 12 l/min and 44 l/min, thereby delivering a medication at a medication mass concentration of at least 5 mg/l and up to 14.5 mg/l.

110. A method for generating a respirable dry powder aerosol 15 from a liquid solution or liquid suspension at a respirable system output volume flow 91, comprising:
   feeding liquid solution or liquid suspension and nozzle heliox 2 into a liquid aerosol generating nozzle 3;
   outputting from the liquid aerosol generating nozzle 3 a liquid aerosol 13 suspended in the nozzle heliox 2 into a cylindrical evaporation chamber 6;
   feeding dilution heliox 4 into the cylindrical evaporation chamber 6; and
   outputting from the cylindrical evaporation chamber 6 a first intermediate dry powder aerosol 14 having fine dry powder particles that allow respirable particles containing a medically active agent and are suspended in gas at a first intermediate dry powder aerosol volume flow 89 and a first intermediate dry powder aerosol particle concentration 90
   feeding the first intermediate dry powder aerosol 14 into a cylindrical radial multi-slit aerosol concentrator 24 comprising at least 3 slits extending from a position at or close to a center of the cylindrical radial multi-slit aerosol concentrator 24 to a position more remote from the center of the cylindrical radial multi-slit aerosol concentrator 24; and outputting the respirable dry powder aerosol 15 at the respirable dry powder aerosol volume flow 91 that is lower than the first intermediate dry powder aerosol volume flow 14 and a respirable dry powder aerosol particle concentration 92 that is higher than the first intermediate dry powder aerosol particle concentration 90.

111. The method according to embodiment 110 further comprising generating the first intermediate dry powder aerosol volume flow 89 at between 80 and 200 l/min.

112. The method according to one of the preceding embodiments 110-111 further comprising providing a surfactant as a constituent of the liquid solution or liquid suspension.

113. The method according to one of the preceding embodiments 110-112 further comprising outputting from the cylindrical evaporation chamber 6 the first intermediate dry powder aerosol 14 at a fine particles of a size of 1.5-4 μm MMAD suspended in gas.

114. The method according to one of the preceding embodiments 110-113 further comprising aerosolizing the liquid solution or liquid suspension having a liquid solution or liquid suspension viscosity of 4 to 39 cSt.

115. The method according to one of the preceding embodiments 110-114 further comprising supplying the nozzle heliox 2 at a nozzle heliox 2 pressure between 207 and 414 kPa.

116. The method according to one of the preceding embodiments 110-115 further comprising generating the respirable dry powder aerosol 15 at a respirable dry powder aerosol pressure of less than 1 cm of water.

117. The method according to one of the preceding embodiments 110-116 further comprising generating the respirable dry powder aerosol volume flow 91 at 10-15 l/min while concentration efficiency is greater than 30%.

118. The method according to one of the preceding embodiments 110-117 further comprising omitting any flow controls at the cylindrical radial multi-slit aerosol concentrator exhaust port 54 of the cylindrical radial multi-slit aerosol concentrator 24.

119. The method according to one of the preceding embodiments 110-118 further comprising providing a counter flow tube 54, an infrared radiation source 39, a reflector 72, and an aerosol collection cone 79.

120. The method according to one of the preceding embodiments 110-119 further comprising supplying the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 μm or less.

121. The method according to embodiment 120 further comprising supplying the liquid solution or liquid suspension at a liquid solution or suspension viscosity exceeding 4 cSt.

122. The method according to embodiment 121 wherein the method is designed to output the respirable dry powder aerosol volume flow 91 between 12 l/min and 44 l/min, thereby delivering a medication at a medication mass concentration of at least 5 mg/l and up to 14.5 mg/l.

123. The method according to one of the preceding embodiments 110-122 further comprising controlling the volume flow ratio such that the ratio of the first intermediate dry powder aerosol volume flow 89 to the respirable dry powder volume flow 91 is less than 5.

124. An aerosol generating system for generating a respirable dry powder aerosol 15 from a liquid solution or liquid suspension, comprising:

a liquid aerosol generating nozzle 3 having a nozzle input end 11 designed to receive the liquid solution or liquid suspension, and having a nozzle heliox supply 55 designed to receive nozzle heliox 2, the liquid aerosol generating nozzle 3 further having a nozzle output end 36 for outputting a liquid aerosol 13 suspended in the nozzle heliox 2; and a cylindrical evaporation chamber 6 having a cylindrical evaporation chamber input end 7 that is connected to the nozzle output end 36 and connected to a dilution heliox supply 60 for receiving both the liquid aerosol 13 suspended in the nozzle heliox 2 and for receiving the dilution heliox 4, and the cylindrical evaporation chamber 6 having a cylindrical evaporation chamber output end 8 outputting a first intermediate dry powder aerosol 14 at a first intermediate dry powder aerosol volume flow 89 and a first intermediate dry powder aerosol particle concentration 90.

125. The system according to embodiment 124 wherein the first intermediate dry powder aerosol volume flow 89 is between 80 and 200 l/min.

126. The system according to one of the preceding embodiments 124-125 wherein the liquid solution or liquid suspension contains a surfactant.

127. The system according to one of the preceding embodiments 124-126 wherein the system is designed to output from the cylindrical evaporation chamber 6 the first intermediate dry powder aerosol 14 having fine particles of a size of 1.5-4 μm MMAD suspended in gas.

128. The system according to one of the preceding embodiments 124-127 wherein the system is designed to aerosolize the liquid solution or liquid suspension having a liquid solution or liquid suspension viscosity of 4 to 39 cSt.

129. The system according to one of the preceding embodiments 124-128 wherein the nozzle heliox 2 has a nozzle heliox pressure between 207 and 414 kPa.

130. The system according to one of the preceding embodiments 124-129 further comprising a counter flow tube 54, an infrared radiation source 39, a reflector 72, and an aerosol collection cone 95.

131. The system according to one of the preceding embodiments 124-130 wherein the system is designed to receive the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 μm or less.

132. The system according to embodiment 131 wherein the system is designed to receive the liquid solution or liquid suspension at a liquid solution or suspension viscosity exceeding 4 cSt.

133. A method for generating a respirable dry powder aerosol 15 from a liquid solution or liquid suspension, comprising:

feeding liquid solution or liquid suspension and nozzle heliox 2 into a liquid aerosol generating nozzle 3;

outputting from the liquid aerosol generating nozzle 3 a liquid aerosol 13 suspended in the nozzle heliox 2 into a cylindrical evaporation chamber 6;

feeding dilution gas 4 into the cylindrical evaporation chamber 6; and outputting from the cylindrical evaporation chamber 6 a first intermediate dry powder aerosol 14 having fine dry powder particles that allow respirable particles containing a medically active agent and are suspended in gas at a first intermediate dry powder aerosol volume flow 89 and a first intermediate dry powder aerosol particle concentration 90.

134. The method according to embodiment 133 further comprising generating the first intermediate dry powder aerosol volume flow 89 at between 80 and 200 l/min.

135. The method according to one of the preceding embodiments 133-134 further comprising providing a surfactant as a constituent of the liquid solution or liquid suspension.

136. The method according to one of the preceding embodiments 133-135 further comprising outputting from the cylindrical evaporation chamber 6 the first intermediate dry powder aerosol 14 at a fine particles of a size of 1.5-4 μm MMAD suspended in gas.

137. The method according to one of the preceding embodiments 133-136 further comprising aerosolizing the liquid solution or liquid suspension having a liquid solution or liquid suspension viscosity of 4 to 39 cSt.

138. The method according to one of the preceding embodiments 133-137 further comprising supplying the nozzle heliox 2 at a nozzle heliox 2 pressure between 207 and 414 kPa.

139. The method according to one of the preceding embodiments 133-138 further comprising providing a counter flow tube 54, an infrared radiation source 39, a reflector 72, and an aerosol collection cone 79.

140. The method according to one of the preceding embodiments 133-139 further comprising supplying the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 μm or less.

141. The method according to one of the preceding embodiments 133-140 further comprising supplying the liquid solution or liquid suspension at a liquid solution or suspension viscosity exceeding 4 cSt.

LIST OF REFERENCE NUMERALS nozzle gas 2
liquid aerosol generating nozzle 3
dilution gas 4
flow distributor 5
cylindrical evaporation chamber 6
cylindrical evaporation chamber input end 7
cylindrical evaporation chamber output end 8
cylindrical single linear slit aerosol concentrator 9
cylindrical single linear slit aerosol concentrator input end 10
nozzle input end 11
liquid aerosol 13
first intermediate dry powder aerosol 14
respirable dry powder aerosol 15
first exhaust aerosol 16
second intermediate dry powder aerosol 17
converging cylindrical single linear slit aerosol concentrator input channel 19
cylindrical single linear slit aerosol concentrator input orifice 20
cylindrical single linear slit aerosol concentrator output orifice 21
diverging cylindrical single linear slit aerosol concentrator output channel 22
cylindrical radial multi-slit aerosol concentrator 24
cylindrical radial multi-slit aerosol concentrator input end 25
cylindrical radial multi-slit aerosol concentrator output end 26
nozzle holder 27
central channel 28
fluid nozzle 29
gas entrance orifice 30
gas channels 31
circumferential pressure equalization chamber 32
circumferential converging channel 33
circumferential diverging channel 34
aerosolizing space 35
nozzle output end 36
aerosol plume 37
counter flow orifice 38
infrared source 39
cylindrical single linear slit aerosol concentrator aerosol separation space 40
circular exit 41
sculptured plenum 43
cylindrical single linear slit aerosol concentrator exhaust port 44
radially aligned acceleration nozzles 45
radially aligned deceleration nozzles 46
acceleration slit orifices 47
deceleration slit orifices 48
cylindrical radial multi-slit aerosol concentrator aerosol separation space 49
circular plenum 50
cylindrical radial multi-slit aerosol concentrator exhaust ports 51
converging cylindrical single linear slit aerosol concentrator input channel angle 52
diverging cylindrical single linear slit aerosol concentrator output channel angle 53
counter-flow tube 54
nozzle gas supply 55
channel 56
compressed gas channel 57
constriction orifice 58
counter flow channel 59
dilution gas supply 60
donut shaped chamber 61
holes in a first baffle 62
first baffle 63
second circular chamber 64
second baffle 65
holes in an inner cylindrical chamber 66
inner cylindrical chamber 67
central holes 68
peripheral holes 69
quartz tube 70
half cylinder aluminum reflector 72
lip-seals 73
converging cylindrical single linear slit aerosol concentrator input orifice angle 74
diverging cylindrical single linear slit aerosol concentrator output orifice angle 75
external surface of the converging channel 76
external surface of the diverging channel 77
internal wall 78
collection cone 79 sculptured exhaust channel 80
entrance plate 81
entrance plate channels 82
rear plate 83
rear plate channels 84
converging exhaust channels 85
second exhaust aerosol 86
first intermediate dry powder aerosol volume flow 89
first intermediate dry powder aerosol particle concentration 90
respirable dry powder aerosol volume flow 91
respirable dry powder aerosol particle concentration 92
second intermediate dry powder aerosol volume flow 93
second intermediate dry powder aerosol particle concentration 94
two-stage concentrator 96

The invention claimed is:

1. An aerosol generating system for generating a respirable dry powder aerosol from a liquid solution or liquid suspension, comprising:
   a liquid aerosol generating nozzle having a nozzle input end designed to receive the liquid solution or liquid suspension, and having a first heliox supply designed to receive a first heliox volume flow, the liquid aerosol generating nozzle further having a nozzle output end for outputting a liquid aerosol suspended in the first heliox volume flow; and
   a cylindrical evaporation chamber having a cylindrical evaporation chamber input end that is connected to the nozzle output end and connected to a second heliox supply for receiving both the liquid aerosol suspended in the first heliox volume flow and for receiving a second heliox volume flow diluting the liquid aerosol suspended in the first heliox volume flow, and the cylindrical evaporation chamber having a cylindrical evaporation chamber output end outputting a first intermediate dry powder aerosol at a first intermediate dry powder aerosol volume flow and a first intermediate dry powder aerosol particle concentration; and at least one of
   i) a cylindrical single linear slit aerosol concentrator having a cylindrical single linear slit aerosol concentrator input end that is connected to the cylindrical evaporation chamber output end, the cylindrical single linear slit aerosol concentrator comprising a converging cylindrical single linear slit aerosol concentrator input channel converging from the cylindrical single linear slit aerosol concentrator input end to a cylindrical single linear slit aerosol concentrator input orifice that is connected to a cylindrical single linear slit aerosol concentrator aerosol separation space, the cylindrical single linear slit aerosol concentrator aerosol separation space connecting both to a cylindrical single linear slit aerosol concentrator exhaust port and to a cylindrical single linear slit aerosol concentrator output orifice, the cylindrical single linear slit aerosol concentrator output orifice being connected to a cylindrical single linear slit aerosol concentrator output channel; and
   ii) a cylindrical radial multi-slit aerosol concentrator comprising a plurality of slits extending from a position at or close to a center of the cylindrical radial multi-slit aerosol concentrator to a position more remote from the center of the cylindrical radial multi-slit aerosol concentrator, the cylindrical radial multi-slit aerosol concentrator having a cylindrical radial multi-slit aerosol concentrator input end that is connected to the cylindrical evaporation chamber output end, and a cylindrical radial multi-slit aerosol concentrator output end; wherein
   the cylindrical single linear slit aerosol concentrator output channel or cylindrical radial multi-slit aerosol concentrator output end output the respirable dry powder aerosol at the respirable dry powder aerosol volume flow that is lower than the first intermediate dry powder aerosol volume flow and a respirable dry powder aerosol particle concentration that is higher than the first intermediate dry powder aerosol particle concentration.

2. The system according to claim 1 wherein the first intermediate dry powder aerosol volume flow is between 80 and 200 l/min.

3. The system according to claim 1 wherein the liquid solution or liquid suspension contains a surfactant.

4. The system according to claim 1 wherein the system is designed to output from the cylindrical evaporation chamber the first intermediate dry powder aerosol having fine particles of a size of 1.5-4 μm MMAD suspended in gas.

5. The system according to claim 1 wherein the system is designed to aerosolize the liquid solution or liquid suspension having a liquid solution or liquid suspension viscosity of 4 to 39 cSt.

6. The system according to claim 1 wherein the first heliox volume flow has a heliox pressure between 207 and 414 kPa.

7. The system according to claim 1 wherein the respirable dry powder aerosol has a respirable dry powder aerosol pressure of less than 1 cm of water.

8. The system according to claim 1 wherein the respirable dry powder aerosol volume flow is 10-15 l/min while concentration efficiency is greater than 50%.

9. The system according to claim 1 wherein the system is free of flow controls at a cylindrical radial multi-slit aerosol concentrator exhaust port of the cylindrical radial multi-slit aerosol concentrator.

10. The system according to claim 1 further comprising a counter flow tube, an infrared radiation source, a reflector, and an aerosol collection cone.

11. The system according to claim 1 wherein the system is designed to receive the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 μm or less.

12. The system according to claim 11 wherein the system is designed to receive the liquid solution or liquid suspension at a liquid solution or suspension viscosity exceeding 4 cSt.

13. The system according to claim 12 wherein the system is designed to output the respirable dry powder aerosol volume flow between 12 l/min and 44 l/min, thereby delivering a medication at a medication mass concentration of at least 5 mg/l and up to 14.5 mg/l.

14. A method for generating a respirable dry powder aerosol from a liquid solution or liquid suspension at a respirable system output volume flow, comprising:
   feeding liquid solution or liquid suspension and a first heliox volume flow into a liquid aerosol generating nozzle;
   outputting from the liquid aerosol generating nozzle a liquid aerosol suspended in the first heliox volume flow into a cylindrical evaporation chamber;

feeding a second heliox volume flow into the cylindrical evaporation chamber diluting the liquid aerosol suspended in the first heliox volume flow; and outputting from the cylindrical evaporation chamber a first intermediate dry powder aerosol having fine dry powder particles that allow respirable particles containing a medically active agent and are suspended in gas at a first intermediate dry powder aerosol volume flow and a first intermediate dry powder aerosol particle concentration feeding the first intermediate dry powder aerosol into at least one of
  i) a cylindrical radial multi-slit aerosol concentrator comprising a plurality of slits extending from a position at or close to a center of the cylindrical radial multi-slit aerosol concentrator to a position more remote from the center of the cylindrical radial multi-slit aerosol concentrator, and
  ii) a cylindrical single linear slit aerosol concentrator having a cylindrical single linear slit aerosol concentrator input end that is connected to the cylindrical evaporation chamber output end, the cylindrical single linear slit aerosol concentrator comprising a converging cylindrical single linear slit aerosol concentrator input channel converging from the cylindrical single linear slit aerosol concentrator input end to a cylindrical single linear slit aerosol concentrator input orifice that is connected to a cylindrical single linear slit aerosol concentrator aerosol separation space, the cylindrical single linear slit aerosol concentrator aerosol separation space connecting both to a cylindrical single linear slit aerosol concentrator exhaust port and to a cylindrical single linear slit aerosol concentrator output orifice, the cylindrical single linear slit aerosol concentrator output orifice being connected to a cylindrical single linear slit aerosol concentrator output channel; and outputting the respirable dry powder aerosol at the respirable dry powder aerosol volume flow that is lower than the first intermediate dry powder aerosol volume flow and a respirable dry powder aerosol particle concentration that is higher than the first intermediate dry powder aerosol particle concentration.

15. The method according to claim 14 further comprising generating the first intermediate dry powder aerosol volume flow at between 80 and 200 l/min.

16. The method according to claim 14 further comprising providing a surfactant as a constituent of the liquid solution or liquid suspension.

17. The method according to claim 14 further comprising outputting from the cylindrical evaporation chamber (6) the first intermediate dry powder aerosol at a fine particles of a size of 1.5-4 μm MMAD suspended in gas.

18. The method according to claim 14 further comprising aerosolizing the liquid solution or liquid suspension having a liquid solution or liquid suspension viscosity of 4 to 39 cSt.

19. The method according to claim 14 further comprising supplying the first heliox volume flow at a heliox pressure between 207 and 414 kPa.

20. The method according to claim 14 further comprising generating the respirable dry powder aerosol at a respirable dry powder aerosol pressure of less than 1 cm of water.

21. The method according to claim 14 further comprising generating the respirable dry powder aerosol volume flow at 10-15 l/min while concentration efficiency is greater than 50%.

22. The method according to claim 14 further comprising omitting any flow controls at the cylindrical radial multi-slit aerosol concentrator exhaust port of the cylindrical radial multi-slit aerosol concentrator.

23. The method according to claim 14 further comprising providing a counter flow tube, an infrared radiation source, a reflector, and an aerosol collection cone.

24. The method according to claim 14 further comprising supplying the liquid solution or liquid suspension at a liquid solution or liquid suspension volume flow of 0.1-3 ml/min, delivering a medication at a medication mass flow rate of at least 150 mg/min in form of the solid particles having a dry powder aerosol mass median aerodynamic diameter (MMAD) of 3 μm or less.

25. The method according to claim 24 further comprising supplying the liquid solution or liquid suspension at a liquid solution or suspension viscosity exceeding 4 cSt.

26. The method according to claim 25 wherein the method is designed to output the respirable dry powder aerosol volume flow between 12 l/min and 44 l/min, thereby delivering a medication at a medication mass concentration of at least 5 mg/l and up to 14.5 mg/l.

27. The method according to claim 14 further comprising controlling the volume flow ratio such that the ratio of the first intermediate dry powder aerosol volume flow (89) to the respirable dry powder volume flow is less than 5.

* * * * *